(12) United States Patent
Wren et al.

(10) Patent No.: US 12,048,743 B2
(45) Date of Patent: Jul. 30, 2024

(54) GLYCONJUGATE VACCINES

(71) Applicants: London School of Hygiene & Tropical Medicine, London (GB); UCL Business LTD, London (GB)

(72) Inventors: Brendan Wren, London (GB); Jeremy Brown, London (GB); Jon Cuccui, London (GB)

(73) Assignee: London School of Hygiene & Tropical Medicine and UCL Business LTD, London (GB)

( * ) Notice: Subject to any disclaimer, the term of this patent is extended or adjusted under 35 U.S.C. 154(b) by 541 days.

(21) Appl. No.: 17/052,485

(22) PCT Filed: May 2, 2019

(86) PCT No.: PCT/EP2019/061266
§ 371 (c)(1),
(2) Date: Nov. 2, 2020

(87) PCT Pub. No.: WO2019/211386
PCT Pub. Date: Nov. 7, 2019

(65) Prior Publication Data
US 2023/0241208 A1 Aug. 3, 2023

(30) Foreign Application Priority Data

May 3, 2018 (EP) ...................................... 1807303

(51) Int. Cl.
| | |
|---|---|
| *A61K 39/09* | (2006.01) |
| *A61K 39/00* | (2006.01) |
| *A61K 39/385* | (2006.01) |
| *A61K 47/64* | (2017.01) |
| *A61P 31/04* | (2006.01) |
| *C07K 14/315* | (2006.01) |

(52) U.S. Cl.
CPC .......... *A61K 39/385* (2013.01); *A61K 39/092* (2013.01); *A61K 47/646* (2017.08); *A61P 31/04* (2018.01); *C07K 14/3156* (2013.01); *A61K 2039/6087* (2013.01)

(58) Field of Classification Search
None
See application file for complete search history.

(56) References Cited

U.S. PATENT DOCUMENTS

| | | | | |
|---|---|---|---|---|
| 11,576,958 | B2 * | 2/2023 | Malley | ............... C07K 14/3156 |
| 2012/0135037 | A1 | 5/2012 | Mizel et al. | |

FOREIGN PATENT DOCUMENTS

| | | |
|---|---|---|
| WO | 2006032499 A1 | 3/2006 |
| WO | 2017216286 A1 | 12/2017 |

OTHER PUBLICATIONS

Brendan Wren: "Development of low cost recombinant glycoconjugate vaccines", Nov. 26, 2018 (Nov. 26, 2018), XP055612404, Retrieved from the Internet: URL:https://www.tm.mahidol.ac.th/research/News &Events/ 2018_ 11_26/2018_ 11 _26.pdf [retrieved on Aug. 12, 2019].
Emily J. Kay et al: "Recombinant expression of *Streptococcus pneumoniae* capsular polysaccharides in *Escherichia coli*", Open Biology, vol. 6, No. 4, Apr. 1, 2016 (Apr. 1, 2016), p. 150243, XP055525931, DOI: 10.1098/rsob.150243 cited in the application.
J. Cuccui et al: "Exploitation of bacterial N-linked glycosylation to develop a novel recombinant glycoconjugate vaccine against Francisella tularensis", The Journal of Infectious Diseases, vol. 205, No. 7, May 22, 2013 (May 22, 2013), pp. 1056-130002, XP055107342, ISSN: 0022-1899, DOI: 10.1098/rsob.130002.
J. S. Brown et al: "Immunization with Components of Two Iron Uptake ABC Transporters Protects Mice against Systemic *Streptococcus pneumoniae* Infection", Infection and Immunity, vol. 69, No. 11, Nov. 1, 2001 (Nov. 1, 2001), pp. 6702-6706, XP055468471, US ISSN: 0019-9567, DOI: 10.1128/IAI. 69.11.6702-6706.2001 cited in the application.
Jon Cuccui et al: "Hijacking bacterial glycosylation for the production of glycoconjugates, from vaccines to humanised glycoproteins", Journal of Pharmacy and Pharmacology, vol. 67, No. 3, Sep. 22, 2014 (Sep. 22, 2014), pp. 338-350, XP055333703, London; GB ISSN: 0022-3573, DOI: 10.1111 /jphp.12321.
Kuo et al: "Characterization of a recombinant pneumolysin and its use as a protein carrier for pneumococcal type 18C conjugate vaccines.", Infection and Immunity, vol. 63, No. 7, Jul. 1, 1995 (Jul. 1, 1995), pp. 2706-2713, XP055033057, ISSN: 0019-9567, cited in the application.
Mark Reglinski et al: "A recombinant conjugated pneumococcal vaccine that protects against murine infections with a similar efficacy to Prevnar-13", NPJ Vaccines, vol. 3, No. 1, Oct. 31, 2018 (Oct. 31, 2018), XP055612400, DOI: 10.1038/ s41 541-01 8-0090-4.
PCT International Search Report with International Application No. PCT/EP2019/061266, Filing date: May 2, 2019, pp. 1-6.
PCT Written Opinion of the International Searching Authority, International Application No. PCT/EP2019/061266, Filing date May 2, 2019, pp. 1-12.
Wacker Michael et al: "Prevention of *Staphylococcus aureus* Infections by Glycoprotein Vaccines Synthesized in *Escherichia coli*", Journal of Infectious Diseases. JID, University of Chicago Press, US, vol. 209, May 1, 2014 (May 1, 2014), pp. 1551-1561, XP009181722, ISSN: 0022-1899, DOI: 10.1093/ INFDIS/JIT800.
Jomaa et al. "Antibodies to the Iron Uptake ABC Transporter Lipoproteins PiaA and PiuA Promote Opsonophagocytosis of *Streptococcus pneumoniae*" Infection and Immunity, Oct. 2005, p. 6852-6859.
Whalan et al. "PiuA and PiaA, iron uptake lipoproteins of *Streptococcus pneumoniae*, elicit serotype independent antibody responses following human pneumococcal septicaemia" FEMS Immunology and Medical Microbiology 43 (2005) 73-80.

* cited by examiner

*Primary Examiner* — S. Devi
(74) *Attorney, Agent, or Firm* — Martin Fessenmaier; Umberg Zipser LLP

(57) ABSTRACT

This invention relates to the use of *S. pneumoniae* protein antigens, such as NanA, PiuA and Sp0148, as carriers for immunogenic *S. pneumoniae* capsular polysaccharide. This may be useful for example in glycoconjugate vaccines able to generate a protective immune response against multiple capsular serotypes. Glycoconjugates, vaccine compositions and methods of manufacture and use are provided.

12 Claims, 6 Drawing Sheets

Specification includes a Sequence Listing.

GLYCONJUGATE VACCINES

This application is a US national phase application of International Application with serial number PCT/EP2019/061266, filed 2 May 2019, which claims priority to United Kingdom patent application 1807303.1, filed 3 May 2018.

FIELD

The present invention relates to glycoconjugate vaccines and methods for their production.

SEQUENCE LISTING

The content of the ASCII text file of the sequence listing named 97426PCT1_Sequence_listing_REV002, which is 48,791 Bytes in size, was created on Mar. 10, 2022 and electronically submitted via EFS-Web, is incorporated by reference in its entirety.

BACKGROUND

Streptococcus pneumoniae (the pneumococcus) is an obligate human pathogen that is one of the most common causes of pneumonia, septicaemia and meningitis, and consequently is responsible for a considerable burden of morbidity and mortality worldwide. S. pneumoniae meningitis is of particular concern owing to its high case fatality rate and the reduced quality of life associated with its neurological sequelae, especially amongst children and the elderly.

The introduction of the pneumococcal conjugate vaccine (PCV) has been very effective in reducing the incidence of S. pneumoniae infections, including meningitis caused by vaccine serotypes (1-8). For example, PCV has led to the considerable reduction in S. pneumoniae infections caused by vaccine serotypes in vaccinated children, and also in the unvaccinated adult population due to herd immunity (1, 2, 4, 13). However, the current PCV has three major disadvantages. Firstly, the dominant disease causing serotypes (STs) vary geographically and with age group, yet the existing PCV formulation is fixed and not readily altered. Thus the current PCV has a variable impact on S. pneumoniae incidence amongst different populations and/or diseases (9). For example S. pneumoniae meningitis continues to cause substantial morbidity and mortality worldwide especially in sub-Saharan Africa where a S. pneumoniae meningitis can affects as many as 98 per 100,000 children under one annually (38). Secondly, as there are over 90 S. pneumoniae capsular serotypes and PCV prevents nasopharyngeal colonisation (the bacterium's usual ecological niche) by only 13 of these, the introduction of PCV has been associated with a major expansion of non-vaccine serotypes including amongst meningitis cases (5, 7, 8). The natural competence of the bacterium indicates that the number of S. pneumoniae capsular serotypes is likely to increase further, leading to a coincident increase in disease incidence as the prevalence of non-vaccine serotypes expands (10-13). Thirdly, PCV vaccines are expensive, restricting their use in low and middle-income countries (LMICs), where the burden of disease is heaviest and preventing the vaccine from being cost effective in adults (14, 15). Hence a low cost S. pneumoniae vaccine that prevents childhood and adult disease, is flexible in antigen content to adjust for changes on S. pneumoniae ecology, and provides some form of cross-serotype protection remains a global imperative.

Current manufacture of PCV is expensive and time-consuming, requiring purification of individual capsular polysaccharides and a multistep process of chemical coupling to a protein carrier. The Wren group has pioneered an alternative approach termed Protein Glycan Coupling Technology (PGCT), using a Campylobacter oligosaccharyl-transferase enzyme, CjPglB, to produce recombinant protein/glycan structures in Escherichia coli (16, 17). PGCT requires co-expression in E. coli of the target glycan genes, a gene encoding the carrier protein antigen with additional 'glycotag' sequences to ensure protein/glycan conjugation, and the coupling enzyme CjPglB (18). Vaccine products are produced by a single step $Ni^{2+}$ affinity chromatography procedure from E. coli batch culture that can readily be scaled up for manufacture. In addition, PGCT would allow greater flexibility in the serotypes included within a PCV, allowing the vaccine to be tailored to the dominant serotypes in different target populations and geographical locations, and rapid reformulation in response to changes in S. pneumoniae ecology.

Another advantage of PGCT is that different protein antigens can be readily combined with the capsular antigen. The basic science of chemically conjugated vaccines has scarcely been advanced since their first commercialisation for Haemophilus influenzae type b in 1990. To date, only four major carrier proteins have been licensed in glycoconjugate vaccine formulations; deactivated toxins from Clostridium tetanus and Corynebacterium diphtheria ($CRM_{197}$), and surface expressed proteins of H. influenza (Protein D) and N. meningitidis serogroup B (19, 20). The immunological potential of a wide range of proteins has not been tested, yet the efficiency of the antibody response to the glycan component of a glyconconjugate varies between different peptides (21, 22). Identifying additional proteins that stimulate good antibody responses when fused to glycan antigens could aid development of glycoconjugate vaccines. Using an S. pneumoniae protein antigen as a carrier protein could also provide the additional advantage of inducing an adaptive response to the protein. Multiple S. pneumoniae protein antigens have been described that when used as vaccines can generate protective immunity in animal models through antibody-mediated opsonophagocytosis (23), inhibition of bacterial protein function (24, 25) and by stimulating Th17 cellular responses (26-28), some of which have been taken forward to phase 1 trials in man. Protective S. pneumoniae protein antigens could be used as carrier proteins for a PGCT approach to making a PCV that can result in serotype independent immunity mediated by adaptive immunity to the protein component. Such a vaccine may also have theoretical advantages in preventing meningitis as antibodies to selected surface protein antigens could prevent penetration of the blood brain barrier (29-31).

PCGT has been used to make an effective prototype vaccine against Francisella tularensis (32), and a Shigella flexneri PGCT vaccine has recently completed phase one trials (33). Recently, it was confirmed that PGCT can be used to make glycoconjugates with four different types of S. pneumoniae capsular serotypes, including serotype 4 (17). However, whether or not a PCV made using PGCT can induce protective anti-capsular responses, and has a similar efficacy to existing commercial PCVs has not been established. Furthermore, there are no data on whether S. pneumoniae protein antigens can act as effective carrier proteins for capsular antigen and are also able to stimulate protective responses.

SUMMARY

The present inventors have recognised that S. pneumoniae protein antigens can be used as carriers for an immunogenic S. pneumoniae capsular polysaccharide in a glycoconjugate vaccine that is able to generate a protective immune response against multiple capsular serotypes.

A first aspect of the invention provides a glycoprotein comprising a S. pneumoniae protein antigen glycosylated with an S. pneumoniae capsular polysaccharide.

Preferred S. pneumoniae protein antigens include NanA, PiuA and Sp0148, most preferably PiuA.

A second aspect of the invention provides a vaccine composition comprising one or more glycoproteins of the first aspect.

A third aspect of the invention provides a method of treatment of S. pneumoniae infection comprising;
    administering a glycoprotein of the first aspect or a vaccine composition of the second aspect to an individual in need thereof.

A fourth aspect of the invention provides a glycoprotein of the first aspect or a vaccine composition of the second aspect for use in a method of treatment of S. pneumoniae infection in an individual.

Treatment of S. pneumoniae infection according to the third and fourth aspects may include prophylactic or protective treatment.

Other aspects and embodiments of the invention are described in more detail below.

BRIEF DESCRIPTION OF THE FIGURES

FIGS. 1A-E show anti capsular polysaccharide antibodies were measured using plates coated with purified type 4 capsular polysaccharide. Antiserum from Prevnar-13 (closed circles) and sham vaccinated (open squares) animals were used as controls. FIGS. 1F-H show anti carrier protein antibodies were measured from mice vaccinated with Combo (Sp4) (closed circles) or Combo (open squares) by sandwich ELISA using a monoclonal anti-His capture antibody and recombinant, unglycosylated carrier proteins. Data are displayed as mean±SEM from technical replicates.

FIG. 2C shows immunoblot analysis of concentrated lysate from ST4 and ST2 overnight cultures using pooled antiserum from the glycosylated and unglycosylated vaccine groups. Molecular mass markers are given in kilodaltons.

FIG. 3A shows examples of flow cytometry histograms for antibody deposition on a S. mitis strain expressing the S. pneumoniae serotype 4 capsule termed S. mitis(Sp4) in 10% antiserum from glycosylated (red shading) and unglycosylated (grey shading) vaccine groups. Sham vaccinated serum (dashed line) was included as a control. FIG. 3B shows antibody deposition measured using a flow cytometry assay on S. mitis (Sp4) in 10% murine antiserum (n=8) from glycosylated (closed circles) and unglycosylated (open squares) vaccine groups. Red dots indicate reactions containing reduced antiserum concentrations (5% vs 10%) in high titre samples. *$p<0.05$ Kruskal-Wallis with Dunn's post-test (vs PBS). FIG. 3C shows examples of flow cytometry histograms for antibody deposition on the TIGR4 S. pneumoniae strain in 2% (red shading), 0.2% (grey shading) and 0.02% (dashed line) antiserum from glycosylated vaccine groups. FIG. 3D shows antibody deposition on TIGR4 in pooled antiserum from mice vaccinated with glycosylated or unglycosylated vaccines. Deposition titres were determined using bacteria incubated with decreasing concentrations of Prevnar-13 antiserum to generate a standard curve. Results displayed as mean±SEM from technical replicates.

FIGS. 4A-D show representative histograms and antibody deposition on homologous and heterologous pneumococcal isolates in 1% pooled antiserum from mice vaccinated with glycosylated NanA (grey shading), Sp0148 (red shading) or PiuA (blue shading) or normal mouse serum (dashed line). Black bars represent the percentage of PE+ bacteria and grey bars represent the gMFI of the positive population. Gates were set such that 5-10% of events were PE+ in the NMS reactions to account for strain specific differences in autofluorescence. Data are displayed as mean±SEM from technical replicates. FIG. 4E shows immunofluorescent staining of homologous and heterologous pneumococcal isolates using antiserum from mice vaccinated with the combination vaccine (green channel) and pneumococcal omni serum (red channel).

FIG. 5A shows examples of flow cytometry histograms for fresh human neutrophils incubated with FAM-SE labelled TIGR4 when opsonized in 20% antiserum from glycosylated (red shading) or unglycosylated (grey shading) vaccine groups and 5% baby rabbit complement. Sham vaccinated serum (dashed line) was included as a control. FIG. 5B shows percent association of fresh human neutrophils with TIGR4 when opsonized in 20% antiserum (n=8) from glycosylated (closed circles) or unglycosylated (open squares) vaccine groups and 5% baby rabbit complement. Antiserum from Prevnar-13 (closed circles) and sham vaccinated (open squares) animals were included as controls. *$p<0.05$ Kruskal-Wallis with Dunn's post-test (vs PBS). FIG. 5E shows percent association of fresh human neutrophils with non-type 4 pneumococci when opsonized in 20% antiserum (n=6) from glycosylated (closed circles) or unglycosylated (open squares) vaccine groups and 5% baby rabbit complement. Antiserum from Prevnar-13 (closed circles) and sham vaccinated (open squares) animals were included as controls.

DETAILED DESCRIPTION

Figure 1:
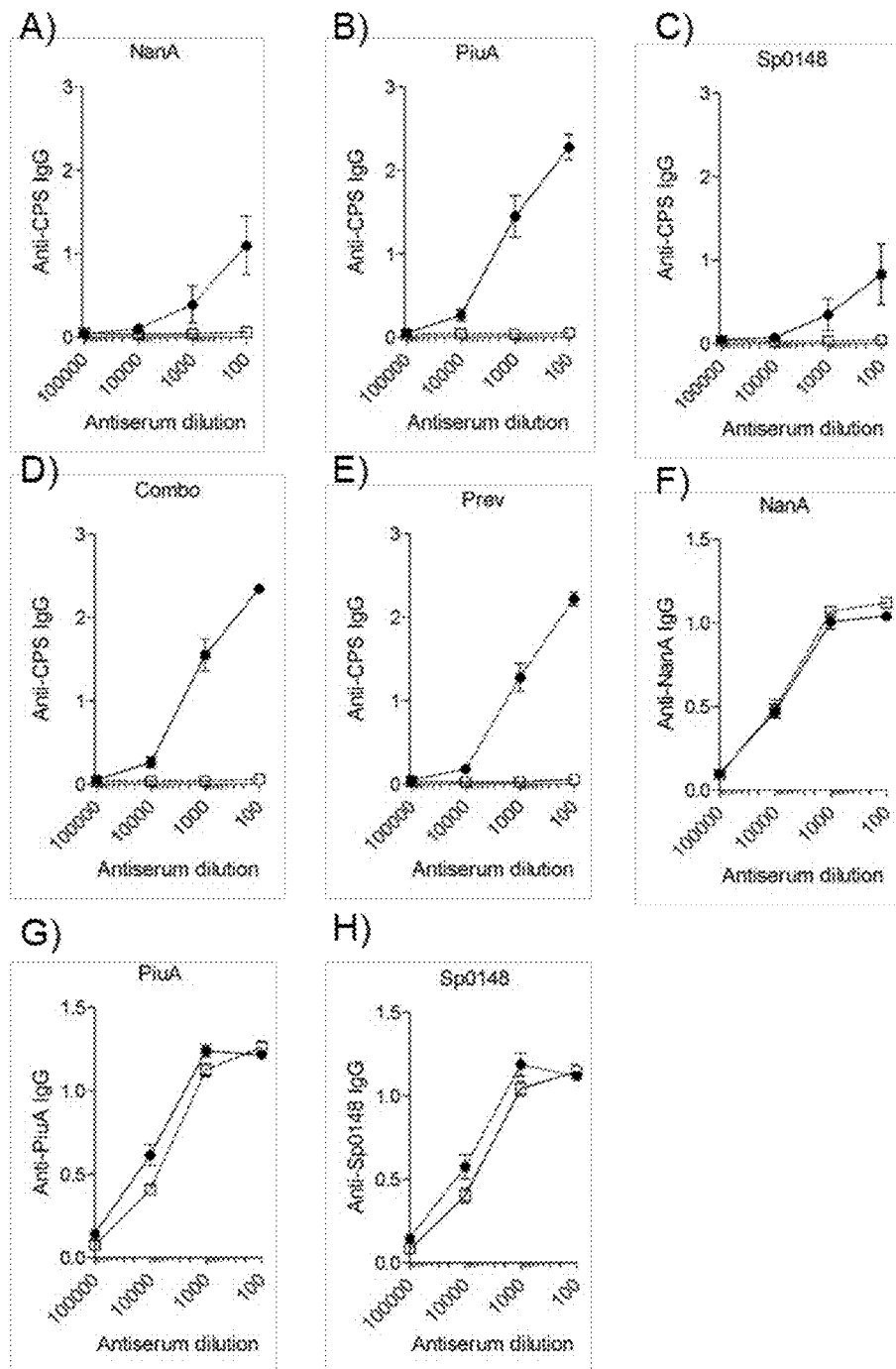
FIG. 1 shows that vaccination with recombinant glycoproteins generates antibodies to the pneumococcal capsule and carrier protein. Antibody levels in antiserum measured from mice (n=8) vaccinated with recombinant glycoproteins (closed circles) or cognate unglycosylated antigens (open squares) by ELISA.

This invention relates to recombinant glycoproteins for use in vaccine compositions, in particular glycoproteins comprising a S. pneumoniae protein antigen glycosylated with a *S. pneumoniae* capsular polysaccharide. These glycoproteins generate protective immune responses against multiple *S. pneumoniae* serovars and may be useful in the preventative or therapeutic treatment of *S. pneumoniae* infections, such as meningitis.

A glycoprotein described herein may comprise a *S. pneumoniae* protein antigen and one or more N-linked *S. pneumoniae* capsular polysaccharides i.e. the capsular polysaccharides may be covalently linked to Asn residues of the protein antigen (N-glycosylation). The capsular polysaccharides and the *S. pneumoniae* protein antigen may be heterologous i.e. the *S. pneumoniae* protein antigen may not be glycosylated with the capsular polysaccharide in natural systems.

Bacterial pathogen cells, such as *S. pneumoniae*, are commonly encapsulated by a polysaccharide capsule which forms a protective outer layer around the cell. Capsule polysaccharide may interact directly with host B cells and induce antibody synthesis in the absence of T-cells. An *S. pneumoniae* capsular polysaccharide may comprise one or more B cell epitopes. The polysaccharides in the capsule are homo- or heteropolymers of monosaccharide sub-units joined by glycosidic linkages. The configuration of the monosaccharide sub-units in the capsular polysaccharide differs between cells of different serotypes of the bacterial pathogen. For example, over 90 different capsular serotypes of *S. pneumoniae* have been identified to date.

An *S. pneumoniae* capsular polysaccharide for use in a glycoprotein described herein may include common *S. pneumoniae* serotypes, such as 1, 3, 4, 5, 6A, 6B, 7F, 9V, 14, 18C, 19A, 19F and 23F. The structures of capsular polysaccharides from *S. pneumoniae* serotypes are well-known in the art (Bentley and Spratt PLoS Genet. 2006 March; 2(3):e31. Epub 2006 Mar. 10).

In some preferred embodiments, the capsular polysaccharide may be a serotype 4 capsular polysaccharide.

A glycoprotein as described herein may comprise one or more capsular polysaccharide moieties, for example two, three, four, five or more capsular polysaccharide moieties. In some embodiments, a glycoprotein may comprise two capsular polysaccharide moieties. For example, capsular polysaccharide moieties may be attached to glycosylation sequons within the glycoprotein, for example at the N and C termini of the protein antigen.

Multiple capsular polysaccharide moieties attached to a glycoprotein may be the same polysaccharide or different polysaccharides.

The *S. pneumoniae* protein antigen may be any protein expressed in *S. pneumoniae* that is capable of eliciting an immune response, preferably a T cell response, in a host. For example, a *S. pneumoniae* protein may comprise one or more T-cell epitopes. Preferred *S. pneumoniae* protein antigens induce cross-protective immunity against multiple strains of *S. pneumoniae* and support strong antibody responses to capsular polysaccharide attached to it.

Suitable *S. pneumoniae* proteins are known in the art and include neuraminidase A (NanA; spr1536; EC3.2.1.18), PiuA (Sp1872), and Sp0148. most preferably PiuA (Sp1872).

A suitable PiuA protein antigen may comprise the amino acid sequence of database accession number KGI34864.1, AOG58833.1, ANO37655.1, KGI33012.1 or SEQ ID NO: 3 or a fragment or variant of any one of these.

A suitable NanA protein antigen may comprise the amino acid sequence of database accession number NP_359129.1 or SEQ ID NO: 6 or a fragment or variant of any one of these. For example, the protein antigen may comprise the N-terminal lectin-like domain of NanA.

A suitable Sp0148 protein antigen may comprise the amino acid sequence of database accession number ABJ55394.1 or WP_000724951.1 or SEQ ID NO: 9 or a fragment or variant of any one of these.

A variant of a reference polypeptide sequence, such as one of SEQ ID NOs: 3, 6, or 9 may comprise an amino acid sequence having at least 50%, at least 60%, at least 70%, at least 80%, at least 90%, at least 95%, at least 98% or at least 99% sequence identity to the reference polypeptide sequence.

Nucleotide and amino acid sequence identity is generally defined with reference to the algorithm GAP (GCG Wisconsin Package™, Accelrys, San Diego CA). GAP uses the Needleman & Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST, BLASTP or BLASTN (which use the method of Altschul et al., FASTA (which uses the method of Pearson and Lipman, or PSI-Search which uses the Smith-Waterman algorithm), generally employing default parameters [54-56, 75].

A protein antigen may, for example, comprise an amino acid sequence which differs from a reference polypeptide sequence, such as one of SEQ ID NOs: 3, 6, or 9 by insertion, addition, substitution or deletion of 1 amino acid, 2, 3, 4, 5-10, 10-20, 20-30, or 30-40 or more amino acids.

A protein antigen may be a fragment of a reference polypeptide sequence, such as one of SEQ ID NOs: 3, 6, or 9, or a variant of a reference polypeptide sequence. A fragment is a truncated polypeptide consisting of fewer amino acids than the full-length sequence that comprises at least one immunogenic determinant of the full-length sequence and retains immunogenicity. Suitable fragments may comprise at least 100, at least 150, at least 200, at least 250 or at least 300 amino acids of the full-length sequence.

A fragment of a full-length protein antigen is capable of raising an immune response (if necessary, when suitably adjuvanted) that recognises the full-length antigen as well as the *S. pneumoniae* serotype or strain from which the protein antigen was derived and preferably other serotypes or strains. Suitable fragments may for example be identified by in silico modelling of potential immunogenic sites, followed by the generation of panels of fragments, and in vivo testing in mammalian protection models.

Suitable protein antigens for use in vaccine compositions may lack a signal peptide sequence.

The *S. pneumoniae* protein antigen may comprise a glycosylation sequon. A glycosylation sequon is a short sequence of consecutive amino acids within a protein that forms the site of attachment for a polysaccharide moiety. The capsular polysaccharide may be covalently linked to an Asn residue within the glycosylation sequon of the protein antigen.

The choice of glycosylation sequon may depend on the oligosaccaryltransferase used to produce the glycoprotein. A suitable glycosylation sequon recognised by *Campylobacter jejuni* PglB may comprise the sequence D/E-Y-N-X-S/T, where Y and X are any amino acid except P (SEQ ID NO: 11). For example, the glycosylation sequon may comprise the sequence DQNAT (SEQ ID NO: 12). Other glycosylation sequons suitable for use with other oligosaccaryltransferases may be readily determined.

The glycosylation sequon may be heterologous i.e. the sequon may not be naturally present in the sequence of the protein antigen and may be incorporated by recombinant techniques. Suitable methods for incorporating a glycosylation sequon into the sequence of a protein antigen are well-known in the art. In some embodiments, a heterologous glycosylation sequon may be flanked by linker residues, such as one or more G residues, for example G, or GG.

The protein antigen may comprise one glycosylation sequon or multiple glycosylation sequons. For example, a protein antigen may comprise two glycosylation sequons. Conveniently, the glycosylation sequons may be located at the N terminus of the protein antigen (or immediately adjacent to the N terminal leader sequence) or at the C terminus of the protein antigen (or immediately adjacent to the C terminal purification tag).

In some embodiments, a protein antigen may be coupled to a leader peptide to direct secretion of the glycoprotein from cell into the culture medium as a precursor. A range of suitable leader peptides are known in the art and include the DsbA leader sequence MKKIWLALAGLVLAFSASAAQ (SEQ ID NO: 13) or a variant thereof. The leader peptide may be heterologous to the protein antigen i.e. it may be a leader sequence that is not naturally associated with the protein antigen. The leader peptide may be located at the N terminus of the precursor glycoprotein. The leader peptide is removed by post-translational processing after expression of the precursor to generate the glycoprotein.

The glycoprotein may further comprise a purification tag. A purification tag is a heterologous amino acid sequence which forms one member of a specific binding pair. Polypeptides containing the purification tag may be detected, isolated and/or purified through the binding of the other member of the specific binding pair to the polypeptide. For example, the purification tag may form an epitope which is bound by an antibody molecule.

Various suitable purification tags are known in the art, including, for example, MRGS(H)$_6$ (SEQ ID NO: 14), DYKDDDDK (FLAG™) (SEQ ID NO: 15), T7-, S-(KETAAAKFERQHMDS) (SEQ ID NO: 16), poly-Arg (R$_{5-6}$) (SEQ ID NO: 17, SEQ ID NO: 18), poly-His (H$_{6-10}$) (SEQ ID NO: 19, SEQ ID NO: 20, SEQ ID NO: 21, SEQ ID NO: 22, SEQ ID NO: 23), poly-Cys (C$_4$) SEQ ID NO: 24) poly-Phe (F$_{11}$) (SEQ ID NO: 25) poly-Asp (D$_{5-16}$) (SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37), Strept-tag II (WSHPQFEK) (SEQ ID NO: 38), c-myc (EQKLISEEDL) (SEQ ID NO: 39), Influenza-HA tag [66], Glu-Glu-Phe tag [67], Tag. 100 (Qiagen; 12 aa tag derived from mammalian MAP kinase 2), Cruz tag 09™ (MKAEFRRQESDR (SEQ ID NO: 40), Santa Cruz Biotechnology Inc.) and Cruz tag 22™ (MRDALDRLDRLA (SEQ ID NO: 41), Santa Cruz Biotechnology Inc.).

A suitable *S. pneumoniae* protein antigen comprising glycosylation sequons, His tag and leader peptide may comprise the amino acid sequence of any one of SEQ NOs: 2, 5 or 7, or a fragment or variant of any one of these. Also disclosed herein are SEQ NOs: 2, 5 or 7 without the leader peptide and optionally the His tag.

A glycoprotein described above may be produced by any suitable method. Preferably, a glycoprotein is produced by Protein Glycan Coupling Technology (PGCT) (see for example 16-18, 41, 42). For example, a method of producing a glycoprotein as described herein may comprise;
expressing in a microbial cell;
   (i) an oligosaccharyltransferase;
   (ii) a *S. pneumoniae* capsular polysaccharide; and
   (iii) a *S. pneumoniae* protein antigen;
such that the oligosaccharyltransferase glycosylates the pathogen protein antigen with the pathogen capsular polysaccharide to produce the glycoprotein.

The microbial cell may be a prokaryotic cell, preferably an *E. coli* cell.

A microbial cell for the production of a glycoprotein may comprise (i) heterologous nucleic acid encoding an oligosaccharyltransferase, (ii) a heterologous capsular polysaccharide biosynthesis locus and (iii) heterologous nucleic acid encoding a pathogen protein antigen. The heterologous nucleic acids and locus may be present on extrachromosomal plasmids in the microbial cell or may be integrated into the genome of the microbial cell.

The microbial cell may be produced by a method comprising transforming a microbial cell with;
   (i) heterologous nucleic acid encoding an oligosaccharyltransferase;
   (ii) a heterologous *S. pneumoniae* capsular polysaccharide biosynthesis locus; and
   (iii) heterologous nucleic acid encoding a *S. pneumoniae* protein antigen.

Suitable methods of transforming microbial cells are well-known in the art. The heterologous nucleic acids and locus may be contained in one or more vectors, for example plasmids. In some embodiments, the heterologous nucleic acids and locus may all be contained in separate vectors. In other embodiments, two or more of the heterologous nucleic acids and heterologous locus may be contained in the same vector.

The microbial cell may be cultured under standard conditions in a cell culture vessel, such as a bioreactor or fermenter, in order to express the oligosaccharyltransferase, protein antigen and capsular polysaccharide.

Oligosaccharyltransferase (EC 2.4.1.119) catalyses the glycosylation of the Asn residue of a glycosylation sequon of the protein antigen with the capsular polysaccharide. A suitable oligosaccharyltransferase for the attachment of any particular capsular polysaccharide substrate may be readily identified using standard techniques. In some preferred embodiments, the oligosaccharyltransferase may be PglB, preferably a bacterial PglB, such as *Helicobacter pullorum* PglB, *Desulfovibrio desulfuricans* PglB, *Campylobacter lari* PglB, and *Campylobacter jejuni* PglB. A preferred PglB may comprise the amino acid sequence of database accession number ASI87642.1 or YP_002344519.1 or SEQ ID NO: 10 or a variant or fragment thereof.

*S. pneumoniae* protein antigens and *S. pneumoniae* capsular polysaccharides are described in more detail above. An *S. pneumoniae* capsular polysaccharide for attachment using PGCT may be attached to an undecaprenol pyrophosphate lipid anchor. In some embodiments, for example when the oligosaccharyltransferase is *Campylobacter jejuni* PglB, the capsular polysaccharide may comprise a reducing-end sugar containing an acetamido group in the C2 position.

The *S. pneumoniae* capsular polysaccharide may be produced in the microbial cell from a heterologous capsular polysaccharide biosynthesis locus or operon. A polysaccharide biosynthesis locus is a region of the *S. pneumoniae* genome that comprises the genes that are required to generate the capsular polysaccharide in the microbial cell. The polysaccharide biosynthesis locus is located in the *S. pneumoniae* genome between the AliA and DexB genes and has four conserved genes at its N terminal end. Polysaccharide biosynthesis loci for different *S. pneumoniae* serovars have been reported in the art (see for example, Bentley and Spratt PLoS Genet. 2006 March; 2(3):e31. Epub 2006 Mar. 10) and may be identified in any *S. pneumoniae* genome using standard genetic analysis techniques.

The biosynthesis locus for an *S. pneumoniae* capsular polysaccharide may be obtained from cells of an *S. pneumoniae* serovar and cloned into a vector for expression in the microbial cell to generate the capsular polysaccharide. The generation of capsular polysaccharides from heterologous biosynthesis loci in a cell is well-established in in the art (16-18, 41, 42).

The glycoprotein may be isolated and/or purified, after production in the microbial cell. This may be achieved using any convenient method known in the art. Techniques for the purification of recombinant glycoprotein are well-known in the art and include, for example HPLC, FPLC or affinity chromatography. In some embodiments, purification may be performed using an affinity tag on the glycoprotein, as described above.

The glycoprotein may be formulated with a pharmaceutically acceptable excipient and optionally an adjuvant and/or one or more different glycoproteins as described herein, for example to produce an immunogenic formulation or vaccine composition for therapeutic use. Vaccine compositions are described in more detail above Both the capsular polysaccharide and the protein antigen are immunogenic and an adaptive immune response against both capsular polysaccharide and the protein antigen may be elicited in an individual to whom the glycoprotein is administered. The immune response may include T cell dependent immune responses and T-cell independent immune responses, such as antibody production. In some preferred embodiments, a glycoprotein may elicit both T cell dependent immune responses and T-cell independent immune responses.

The glycoprotein may be capable of providing a protective immune response against *S. pneumoniae*. For example, the glycoprotein may stimulate, promote or enhance a protective immune response when the individual is subsequently exposed to *S. pneumoniae*. The glycoprotein may stimulate a protective immune response against the *S. pneumoniae* serotype from which the capsular polysaccharide and/or protein antigen was derived or *S. pneumoniae* serotypes other than the *S. pneumoniae* serotype from which the capsular polysaccharide and/or protein antigen was derived. For example, the glycoprotein may stimulate protective immune responses against multiple *S. pneumoniae* serotypes. In some embodiments, a protective immune response may be serotype independent.

One or more glycoproteins as described above may be formulated into a vaccine composition.

A vaccine composition is an immunogenic formulation comprising one or more immunogenic components that is capable of generating protective immune responses in an individual to the one or more immunogenic components. The immunogenic components of the vaccine composition described herein may be contained in the *S pneumoniae* protein antigens and *S pneumoniae* capsular polysaccharides of the one or more glycoproteins.

The vaccine compositions described herein comprise protein and polysaccharide antigens from *S. pneumoniae* that are capable of eliciting an immune response against *S. pneumoniae* in an individual. The protein and polysaccharide antigens may, for example, be immunoreactive against *S. pneumoniae*-exposed serum, such as *S. pneumoniae* exposed human serum.

A vaccine composition may comprise one glycoprotein as described above or more preferably, multiple glycoproteins, for example 2, 3, 4, 5, 6, 7, 8, 9, 10 or more different glycoproteins. The multiple glycoproteins in the composition may comprise multiple different protein antigens and/or multiple different capsular polysaccharides. For example, the vaccine composition may comprise glycoproteins with multiple different *S. pneumoniae* capsular polysaccharides and the same *S. pneumoniae* protein antigen; multiple different *S. pneumoniae* protein antigens and the same *S. pneumoniae* capsular polysaccharide; or multiple different *S. pneumoniae* protein antigens and multiple different *S. pneumoniae* capsular polysaccharides.

A vaccine composition may further comprise an adjuvant. An adjuvant is a non-immunogenic agent that increases or enhances the immune response to an antigen in an individual (for a review, see, e.g, and Vaccine Adjuvants: adjuvants: preparation methods and research protocols Ed O'Hagan (2000) Springer).

Examples of suitable adjuvants include aluminium and aluminium salts such as aluminium hydroxide and/or aluminium phosphate; oil-emulsion compositions (or oil-in-water compositions), including squalene-water emulsions, such as Emulsigen™ (MVP Technologies Inc), Addavax™ and MF59™ (see, for example WO 90/14837); saponin formulations, such as, for example, QS21 and Immunostimulating Complexes (ISCOMS) (see for example U.S. Pat. No. 5,057,540; WO 90/03184, WO 96/11711, WO 2004/004762, WO 2005/002620); Toll-like receptor (TLR) agonists, such as TLR7 agonists (see for example WO 2012/117377), optionally in combination with an aluminium salt; bacterial or microbial derivatives, such as monophosphoryl lipid A (MPL), 3-O-deacylated MPL (3dMPL), flagellin, CpG-motif-containing oligonucleotides, muramyl dipeptide (MDP) and/or trehalose dicorynomycolate (TDM) ADP-ribosylating bacterial toxins, such as *E. coli* heat labile enterotoxin LT and cholera toxin CT and their non-enzymatic binding subunits, poly I:C, anionic polymers, including acrylic acid polymers, such as polymethylmethacrylate, acrylic acid crosslinked with allyl sucrose (for example Carbopol™, Lubrizol and polyethylene-imine (PEI)), cytokines selected from the group consisting of e.g. GMCSF, interferon gamma, interferon alpha, interferon beta, interleukin 12, interleukin 23, interleukin 17, interleukin 2, interleukin 1, TGF, TNFα, and TNFβ.

A method of making a vaccine composition may comprise;
admixing one or more glycoproteins as described above with a pharmaceutically or veterinarily acceptable excipient and optionally an adjuvant.

The term "pharmaceutically acceptable" or "veterinarily acceptable" as used herein pertains to compounds, materials, compositions, and/or dosage forms which are, within the scope of sound veterinary or medical judgement, suitable for use in contact with the tissues of a subject (e.g. human or other mammal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable excipients and carriers include, without limitation, water, saline, buffered saline, phosphate buffer, alcoholic/aqueous solutions, emulsions or suspensions. Other conventionally employed diluents, adjuvants, and excipients may be added in accordance with conventional techniques. Such carriers can include ethanol, polyols, and suitable mixtures thereof, vegetable oils, and injectable organic esters. Buffers and pH-adjusting agents may also be employed, and include, without limitation, salts prepared from an organic acid or base. Representative buffers include, without limitation, organic acid salts, such as salts of citric acid (e.g., citrates), ascorbic acid, gluconic acid, carbonic acid, tartaric acid, succinic acid, acetic acid, phthalic acid, Tris, trimethylamine hydrochloride, or phosphate buffers. Parenteral carriers can include sodium chloride solution, Ringer's dextrose, dextrose, trehalose, sucrose, lactated Ringer's, or fixed oils. Intravenous carriers can include fluid and nutrient replenishers, electrolyte replenishers, such as those based on Ringer's dextrose, and the like. Preservatives and other additives such as, for example, antimicrobials, antioxidants, chelating agents (e.g., EGTA; EDTA), inert gases, and the like may also be provided in the pharmaceutical carriers. The vaccine compositions described herein are not limited by the selection of the carrier. The preparation of these pharmaceutically-acceptable compositions, from the above-described components, having appropriate pH, isotonicity, stability and other conventional characteristics, is within the skill of the art.

Suitable carriers, excipients, etc. can be found in standard pharmaceutical texts, for example, Remington's Pharmaceutical Sciences [71] and The Handbook of Pharmaceutical Excipients, 4th edit., eds. R. C. Rowe et al, APhA Publications, 2003.

A vaccine composition may conveniently be presented in unit dosage form and may be prepared by any methods well-known in the art of pharmacy. Such methods include the step of bringing the one or more isolated immunogenic polypeptides into association with a carrier or excipient as described above which may constitute one or more accessory ingredients. In general, the formulations are prepared by uniformly and intimately bringing into association the active compound with liquid carriers or finely divided solid carriers or both.

Vaccine compositions described herein may be produced in various forms, depending upon the route of administration. For example, the vaccine compositions can be made in the form of sterile aqueous solutions or dispersions, suitable for injectable use, or made in lyophilized forms using freeze-drying techniques. Lyophilized vaccine compositions are typically maintained at about 4° C., and can be reconstituted in a stabilizing solution, e.g., saline or HEPES, with or without adjuvant. Vaccine compositions can also be made in the form of suspensions or emulsions.

These vaccine compositions may contain additives suitable for administration via any conventional route of administration. The vaccine compositions may be prepared for administration to subjects in the form of, for example, liquids, powders, aerosols, tablets, capsules, enteric-coated tablets or capsules, or suppositories. Thus, the vaccine compositions may also be in the form of, but are not limited to, suspensions, solutions, emulsions in oily or aqueous vehicles, pastes, and implantable sustained-release or biodegradable formulations. Compositions for sustained release or implantation may comprise pharmaceutically acceptable polymeric or hydrophobic materials, such as an emulsion, an ion exchange resin, a sparingly soluble polymer, or a sparingly soluble salt.

Formulations suitable for parenteral administration (e.g. by injection, including intramuscular), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents. Examples of suitable isotonic vehicles for use in such formulations include Sodium Chloride Injection, Ringer's Solution, or Lactated Ringer's Injection. Typically, the concentration of the active compound in the solution is from about 1 µg/ml to about 100 mg/ml, for example, from about 10 µg/ml to about 50 mg/ml. In some formulations for parenteral administration, the active ingredient may be provided in dry (i.e., powder or granular) form for reconstitution with a suitable vehicle (e.g., sterile pyrogen free water) prior to parenteral administration of the reconstituted composition. Other useful parenterally-administrable formulations include those which comprise the active ingredient in microcrystalline form, in a liposomal preparation, or as a component of a biodegradable polymer system.

Vaccine compositions may be presented in unit-dose or multi-dose sealed containers, for example, ampoules and vials, and may be stored in a freeze-dried (lyophilised) condition requiring only the addition of the sterile liquid carrier, for example water for injections immediately prior to use.

The vaccine composition may be administered to a subject by any convenient route of administration. In some embodiments, administration is by parenteral routes, such as intramuscular, intranasal, trans-dermal or sub-cutaneous routes. For example, the vaccine composition may be administered by injection, preferably intramuscular injection.

It will be appreciated that appropriate dosages of the vaccine compositions can vary from individual to individual, or population to population, depending on the circumstances. Determining the optimal dosage will generally involve the balancing of the level of therapeutic benefit against any risk or deleterious side effects of the administration. The selected dosage level will depend on a variety of factors including, but not limited to, the route of administration, the time of administration, the rate of excretion of the vaccine composition, other drugs, compounds, and/or materials used in combination, and the species, breed, maturity, sex, weight, condition and general health of the individual. The amount of vaccine composition and route of administration will ultimately be at the discretion of the veterinary surgeon or physician, although generally the dosage will be to achieve serum concentrations of the vaccine composition which are sufficient to produce a beneficial effect without causing substantial harmful or deleterious side-effects.

Treatment may comprise the administration of a therapeutically effective amount of a vaccine composition to the individual. "Therapeutically effective amount" pertains to that amount of a vaccine composition that is effective for producing some desired therapeutic effect, commensurate with a reasonable benefit/risk ratio. For example, a suitable amount of a vaccine composition for administration to an individual may be an amount that generates a protective immune response against each polysaccharide or protein antigen that is present in the composition in the individual.

An individual to whom a vaccine composition described herein has been administered may display acquired and/or adaptive immune responses against S pneumoniae when subsequently exposed to it. These responses may confer protection against morbidity or mortality caused by infection with S pneumoniae. The vaccine composition may for example, reduce the likelihood of infection with S pneumoniae, reduce the severity or duration of the clinical signs of infection in the individual, prevent or delay the onset of clinical signs of infection or prevent or reduce the risk of the death of the individual following infection with *S pneumoniae*.

Administration in vivo can be effected in one dose, continuously or intermittently (e.g., in divided doses at appropriate intervals). In some embodiments, vaccine compositions may be administered more than once to the same individual with sufficient time interval to obtain a boosting effect in the individual, e.g., at least 1 week, 2 weeks, 3 weeks or 4 weeks, between administrations, preferably about 2 weeks. A prime dose of the vaccine composition may be administered to the individual followed by a booster dose. For example, a prime dose may be administered to a let at 1-4 weeks old and a booster dose at 3-6 weeks old. Methods of determining the most effective means and dosage of administration are well known to those of skill in the art and will vary with the formulation and the subject being treated. For example, in some embodiments, the prime dose of the vaccine composition may be administered when the levels of maternal derived antibodies in the let have declined (e.g. after 2-4 weeks) followed by a booster dose two weeks later. Single or multiple administrations may be carried out with the dose level and pattern being selected by the veterinary surgeon or physician.

A glycoprotein or vaccine composition as described herein may be for use in a method of treatment of the animal or human body. Aspects of the invention provide a glycoprotein or vaccine composition as described herein for use in the treatment of *S. pneumoniae* infection in an individual or population of individuals; the use of a glycoprotein or vaccine composition as described herein for the manufacture of a medicament for use in the treatment of *S. pneumoniae* infection in an individual or population of individuals; and a method of treating *S. pneumoniae* infection comprising administering a glycoprotein or vaccine composition as described herein to an individual or population of individuals in need thereof.

*S. pneumoniae* infection includes infection with *S. pneumoniae* of any serotype or strain, for example *S. pneumoniae* serotype 4, as well as clinical signs of *S. pneumoniae* infection, and conditions associated with *S. pneumoniae* infection, including bacterial meningitis, septicaemia, pneumonia, otitis media, cardiac infections, pericarditis, septic arthritis and spontaneous peritonitis.

*S. pneumoniae* infection may be identified or diagnosed using standard diagnostic criteria.

Treatment as described herein may prime the immune system of the individual or population to generate an immune response upon exposure to *S. pneumoniae*. This may achieve a desired therapeutic effect, for example, increased protection against or resistance to morbidity or mortality caused by *S. pneumoniae* infection.

More preferably, treatment as described herein may be prophylactic or preventative treatment i.e. the individual or population may not be suffering from *S. pneumoniae* infection and/or may not be displaying clinical signs of *S. pneumoniae* infection at the time of treatment. In some embodiments, the individual or population may be susceptible to or at risk of *S. pneumoniae* infection.

For example, the glycoprotein or vaccine composition may be useful in the vaccination or immunisation of an individual or population against *S. pneumoniae*. The treatment of *S. pneumoniae* infection as described herein may prevent subsequent *S. pneumoniae* infection in the individual or population or ameliorate its effects. Prophylactic or preventative treatment may reduce the susceptibility of the individual or population to *S. pneumoniae* infection, prevent or inhibit nasopharyngeal colonisation by *S. pneumoniae*, reduce the risk or likelihood of infection with *S. pneumoniae*, delay or reduce the severity or duration of lesions or other clinical signs of a *S. pneumoniae* infection, or prevent or delay the onset of clinical signs of *S. pneumoniae* in the individual or population, and/or reduce or prevent morbidity or mortality caused by a *S. pneumoniae* infection.

An individual or population suitable for treatment with a glycoprotein or vaccine composition described herein may be human or non-human mammal, for example a non-human mammal susceptible to *S. pneumoniae* infection, including equine mammals, such as horses.

A glycoprotein or vaccine composition described herein may reduce the incidence of *S. pneumonia* related morbidity or mortality in a population relative to unimmunised populations. For example, the incidence of lesions or other clinical signs of *S. pneumonia* infection may be reduced in the immunised population relative to unimmunised populations, following exposure to *S. pneumoniae*. In some embodiments, immunisation of a population with a vaccine composition as described herein may reduce the number of individuals in the population showing clinical signs of *S. pneumoniae* infection by at least 50% more preferably at least 60%, at least 65%, at least 70%, or at least 75%, most preferably at least 80% compared to an untreated population.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Experimental

The following experiments employ PGCT to conjugate an N-terminal fragment of the brain endothelial cell invasin NanA (29), the Th17 stimulating antigen Sp0148 (24) and the ABC transporter PiuA (34), to capsular serotype 4 antigen and test the efficacy of these glycoconjugates using mouse models of vaccination and *S. pneumoniae* infection.

1. Materials and Methods 1.1 Bacterial Strains and Growth Conditions

The bacterial strains used in this study are listed in Table 1. *Escherichia coli* isolates were routinely cultured in modified super optimal broth (SSOB) or agar at 28° C. Where appropriate cultures were supplemented with 100 μg/ml ampicillin, 20 μg/ml tetracycline and/or 80 μg/ml spectinomycin. *S. pneumoniae* were cultured on Columbia horse blood agar plates (E&O laboratories) or in brain heart infusion (BHI) broth at 37° C.+5% $CO_2$. Where appropriate, cultures were supplemented with 5 µg/ml gentamycin or 75 µg/ml streptomycin. *Streptococcus mitis* was cultured in Todd-Hewitt broth supplemented with 0.5% yeast extract at 37° C.+5% $CO_2$. *S. pneumoniae* and *S. mitis* were cultured to an $OD_{600}$ of approximately 0.4-08 and stored in single use 1 ml aliquots at −80° C. in 20% glycerol. Stocking densities were determined by serial dilution and plating.

1.2 Synthesis and Genetic Modification of Carrier Protein Genes

DNA sequences, codon optimised for expression in *E. coli*, encoding neuraminidase A (NanA, Spd1504) and the ABC transporter proteins PiuA (Sp1872) and Sp0148 were synthesized commercially in pUC57 and sub cloned into pEXT21. Owing to the size of full length NanA, which made recombinant production at high yields difficult in early experiments, the N-terminal lectin-like domain of the protein which is essential for protein function, was sub cloned from pEXT21 (nanA) as outlined in the supplementary methods (29). To facilitate PglB glycosylation, synthetic carrier protein sequences were modified with the sequon DQNAT (SEQ ID NO: 12), flanked by two spacer glycine residues, at the N and C terminus of the mature protein. Periplasmic targeting was facilitated by exchanging native signal peptides for the DsbA leader sequence MKKIWLA-LAGLVLAFSASAAQ (SEQ ID NO: 13). C-terminal deca-His sequences were included to facilitate Ni-NTA purification. In NanA, internal EcoRI and XbaI sites were replaced with synonymous mutations. Commercial plasmid constructs were cloned into library efficient DH5α cells (Life Technologies) according to the manufacturer's instructions and stored at −80° C. in 20% glycerol. Synthetic carrier protein sequences were sub cloned in the expression vector pEXT21 using the restriction enzymes EcoRI and XbaI (New England Biolabs).

1.3 Preparation of Expression Strains

*E. coli* W3110 and W311B pB4-4 cell cultures were inoculated 1:100 from overnights and grown to an $OD_{600}$ of 0.3-0.6. Cultures were chilled on ice, pelleted at 4000×g for 10 min and washed sequentially with 0.5 volumes and then 0.25 volumes of ice cold 10% glycerol. Competent cells were resuspended in $1/250^{th}$ volume ice cold 10% glycerol and 50 µl aliquots were transformed with pEXT21 (nanA), pEXT21 (piuA) or pEXT21 (sp0148) in a 0.2 cm gap cuvette at 2.5 kV, 200Ω and 25 µF. To investigate the role of lipid linked Sp4 in the generation of anti-capsule immunity, W3110 pB4-4 cells were transformed with pEXT21 (piuA). Isolates confirmed for expression were stored at −80° C. in 20% glycerol.

1.4 Recombinant Protein Preparation

W3110 pEXT21 (nanA/piuA/sp0148) and W311B pB4-4 pEXT20 pEXT21 (nanA/piuA/sp0148) isolates were cultured overnight at 28° C. and sub cultured 1:100 into SSOB. The bacteria were cultured for 2-3 h prior to overnight induction with 1 mM IPTG and 4 mM $MnCl_2$ at 28° C. The cells were pelleted at 14,000×g and lysed using a pressure cell homogeniser (Stanstead). Lysates were treated with 25 U/ml Benzonase Nuclease (Sigma-Aldrich) for 20 min at RT and 0.2 µm filtered using Millex-GP Syringe Filters (Millipore). In initial studies, recombinant (glyco)proteins were purified using the Ni-NTA purification system (Thermo Fisher Scientific) according to the manufacturer's instructions. For vaccination studies, recombinant (glyco)proteins were isolated using GE Healthcare His-trap FF columns and an AKTA purifier with a linear imidazole gradient of 25 to 250 mM. Fractions containing only recombinant (glyco) proteins were identified by SDS-PAGE and Coomassie staining, pooled and buffer exchanged into PBS using Vivaspin 20 Centrifugal Concentrators (10,000 MWCO). Protein concentrations were determined using the Pierce Coomassie Plus (Bradford) Assay Kit (Thermo Fisher). Recombinant (glyco)proteins were filter sterilised, normalised to 200 µg/ml in PBS and stored at −80° C. Sample purity was confirmed by SDS-PAGE.

1.5 SDS-PAGE and Immunoblotting

Recombinant proteins (10 µl) were combined with 4 µl of 4×LDS sample buffer (thermos fisher) and 2 µl of 0.5 M dithiothreitol (Sigma-Aldrich) and heated to 70° C. for 10 min. Samples were separated on NuPAGE 12% bis-tris protein gels in MOPS buffer and transferred to nitrocellulose membrane using the iblot2 transfer system according to the manufacturer's instructions. Membranes were blocked with PBST supplemented with 2.5% skimmed milk powder (Marvel) and 0.1% normal goat serum (Thermo Fisher). Serotype 4 rabbit anti-capsule antibody (Statens Serum Institut, Denmark) and monoclonal mouse anti-His IgG (Abcam) were used as primary antibodies at a dilution of 1:1000 and 1:5000 respectively. After 1 h incubation membranes were washed three times with PBST and incubated for 45 min with secondary goat anti-rabbit IgG (IRDye800) and goat anti-mouse IgG (IRDye680) conjugate antibody at a dilution of 1:10000. Membranes were washed a further three times in PBST before detection with the LI-COR odyssey fluorescent imaging system (LI-COR Biosciences UK Ltd).

TIGR4 and D39 lysates were prepared by pressure lysis of overnight cultures. Lysates were 0.2 µm filtered and 10× concentrated using Vivaspin 20 Centrifugal Concentrators (10,000 MWCO). 10 µl aliquots of concentrated lysate were analysed by immunoblotting using a 1:1000 dilution of murine antiserum and a 1:10,000 dilution of goat anti-mouse IgG (IRDye800) as outlined above. Densitometry was performed using the LI-COR odyssey fluorescent imaging system.

1.6 Vaccination Studies

Female 5-6-week CD1 mice were purchased from Charles River and housed in cages of 4. For antiserum generation and pneumonia challenge studies mice were vaccinated intraperitoneally with 10 µg of recombinant (glyco)protein emulsified 1:1 in Sigma adjuvant (Sigma-Aldrich) on day 0. Booster immunisations were given subcutaneously on day 21 and 35. Positive control groups were vaccinated and boosted with 20 µl of Prevnar-13 (Wyeth) diluted 1:5 PBS. Negative control groups were sham vaccinated with PBS and Sigma adjuvant alone. Colonisation studies were performed using mice vaccinated intraperitoneally as outlined above and boosted intranasally under light isoflurane anaesthesia with 2 µg of recombinant protein (no adjuvant), or 20 µl of diluted Prevnar-13 or PBS. For pneumonia studies mice were infected with $1\times10^7$ CFU of TIGR4 in 50 µl of PBS under isoflurane anaesthesia. Mice were culled 24 h post infection and bacterial burdens in the lung and blood were assessed.

1.7 Anti-Capsule and Anti-Protein ELISAs

To measure anti-capsule responses, Nunc Maxisorp 96 well plates were coated with 0.5 µg/well purified type 4 pneumococcal polysaccharide (Statens Serum Institut, Denmark) in PBS overnight at 4° C. Wells were blocked with PBST supplemented with 2.5% skimmed milk powder and 0.1% normal goat serum and incubated with 10-fold dilutions of murine antiserum in PBS supplemented with 0.1% BSA and 0.01% sodium azide for 1 h at 28° C. Wells were washed three times with PBST and incubated with a 1:20, 000 dilution of HRP-conjugated goat anti-mouse IgG (Abcam) 1 h at 28° C. Following a further three washes bound antibodies were detected using 50 µl of tetramethylbenzidine. The reaction was halted using 50 µl of 1M $H_2SO_4$ and the $OD_{450}$ was measured using an EL800 Microplate reader (BioTek Instruments) and a reference wavelength of $A_{630}$) Where appropriate anti-capsule antibody titres were determined by comparison to a standard curve generated using anti-Prevnar antiserum with an arbitrary titre of 1:10,000.

Anti-protein responses were measured by sandwich ELISA using plates coated with 0.1 µg of monoclonal rabbit anti-his IgG (Abcam) in PBS overnight at 4° C. Wells were washed three times with PBST and incubated with 1 µg/well of recombinant protein in PBS for 2 h at 28° C. Following a further three washes, plates were blocked and incubated with 10-fold dilutions of murine antiserum and HRP-conjugated goat anti mouse IgG as outlined above.

For whole cell ELISAs, TIGR4 and D39 cultures were grown to an $OD_{600}$ of approximately 0.4-08, washed and resuspended to an $OD_{600}$ of 0.4 in 10% glycerol. Plates were incubated with 100 µl/well of normalised bacteria for 2 h at RT and bacteria were fixed with 4% formaldehyde for 20 min. Plates were washed and incubated with a 1:1000 dilution of murine antiserum for 2 h at 28° C. and HRP-conjugated goat anti mouse IgG as outlined above.

1.8 Antibody Deposition Assays

Antibody deposition assays were performed as previously described using frozen stocks of S. pneumoniae and S. mitis. Briefly, $2 \times 10^6$ CFU/well bacteria were incubated with diluted murine antiserum in a final volume of 50 µl for 30 min at 37° C. with agitation at 225 rpm. The bacteria were pelleted at 3000 rpm, washed twice with PBS and incubated for a further 30 min with a 1:100 dilution of PE-conjugate goat anti mouse IgG (25 µl/well). Following a further two washes, the bacteria were fixed with 200 µl/well of 4% paraformaldehyde and the fluorescence intensity of the bacterial population was measured by flow cytometry using the FACSVerse system. TIGR4 deposition titres were determined by comparison to a standard curve, generated using anti-Prevnar antiserum with an arbitrary titre of 1:10,000.

1.9 Opsonophagocytic Uptake Assays

Opsonophagocytic uptake assays were performed using neutrophils purified from healthy human donors using the MACSexpress magnetic purification system according to the manufacturer's instructions. Frozen stocks of S. pneumoniae were resuspended in 1 ml of 0.1 M sodium bicarbonate and incubated with FAM-SE for 30 min at 37° C. The bacteria were washed three times with PBS and $2 \times 10^6$ CFU/well bacteria were incubated with diluted murine antiserum in a final volume of 50 µl for 30 min at 37° C. with agitation at 225 rpm. $2 \times 10^4$ neutrophils were added per well in 50 µl of PBS and the reactions were incubated for a further 30 min. The reactions were fixed with 100 µl/well 4% paraformaldehyde and the fluorescence intensity of the neutrophil population was measured by flow cytometry using the FACSVerse system.

1.10 Statistical Analysis

Statistical analyses, appropriate for the group size and number of comparisons, were performed using GraphPad Prism. Flow cytometry data analysis was performed using FlowJo software.

1.11 Recombinant Protein Production

The N-terminal lectin-like domain of NanA was subcloned from pEXT21 (nanA) using the primers listed in Table S2. Two fragments of the commercially synthesised NanA construct were amplified from pEXT21 (nanA) using Q5 High-Fidelity 2× Master Mix (New England Biolabs) and the primer pairs pEXT-F/nanA-R and pEXT-R/nanA-F with the conditions: 98° C. 10 s, 60° C. 30 s, 72° C. 30 s for 30 cycles. Fragments were PCR purified (QIAquick PCR Purification Kit, Qiagen) and digested with AvrII (New England Biolabs). Digested fragments were PCR purified and ligated using T3 DNA ligase (New England Biolabs). The religated reaction mixture was used as the template for NanA (N-terminus) amplification using the pEXT-F/pEXT-R primer pair as outlined above. The resulting insert was PCR purified and cloned into pEXT21 using the restriction enzymes EcoRI and XbaI. Plasmid pEXT21 (NanA), containing the lectin-like domain of NanA and the genetic components required for PglB glycosylation and Ni-NTA purification, was transformed into DH5α cells and stored at −80° C. in 20% glycerol.

2. Results 2.1 Vaccination with Recombinant Glycoconjugates Generates Antibodies Against the Capsule and Carrier Protein NanA(Sp4), PiuA(Sp4) and Sp0148(Sp4) were prepared from isolates and used to vaccinate groups of eight F CD1 mice separately (10 µg/mouse/injection) or in combination (4 µg each protein/mouse/vaccination) as outlined above. Cognate unglycosylated antigens, Prevnar-13 and PBS alone (Sham) vaccine groups were included as controls for anti-protein and anti-capsule responses. In serum recovered from mice 7 days after the last vaccination, circulating anti-capsule antibodies were above the limit of detection in all glycosylated antigen groups, with no reactivity detected in groups vaccinated with protein alone (FIG. 1A-E). Anti-capsule antibody levels varied markedly between groups but did not appear to correlate with the relative levels of glycoprotein present within the different preparations. While the highest level of glycosylation occurred in the NanA samples, PiuA glycoconjugates stimulated the most robust anti-capsular immune responses (FIG. 1A). Vaccination with all three glycoconjugates combined generated a strong anti-capsule response that was similar to the response generated with Prevnar-13. Anti-carrier protein responses were assessed by sandwich ELISA and confirmed that all vaccine groups had seroconverted to the selected carrier proteins (FIG. 1F-H). Strong humoral immune responses were generated to the protein antigens regardless of whether they carried the serotype 4 glycan, indicating that glycosylation had no discernible effect on protein antigenicity.

Figure 2:
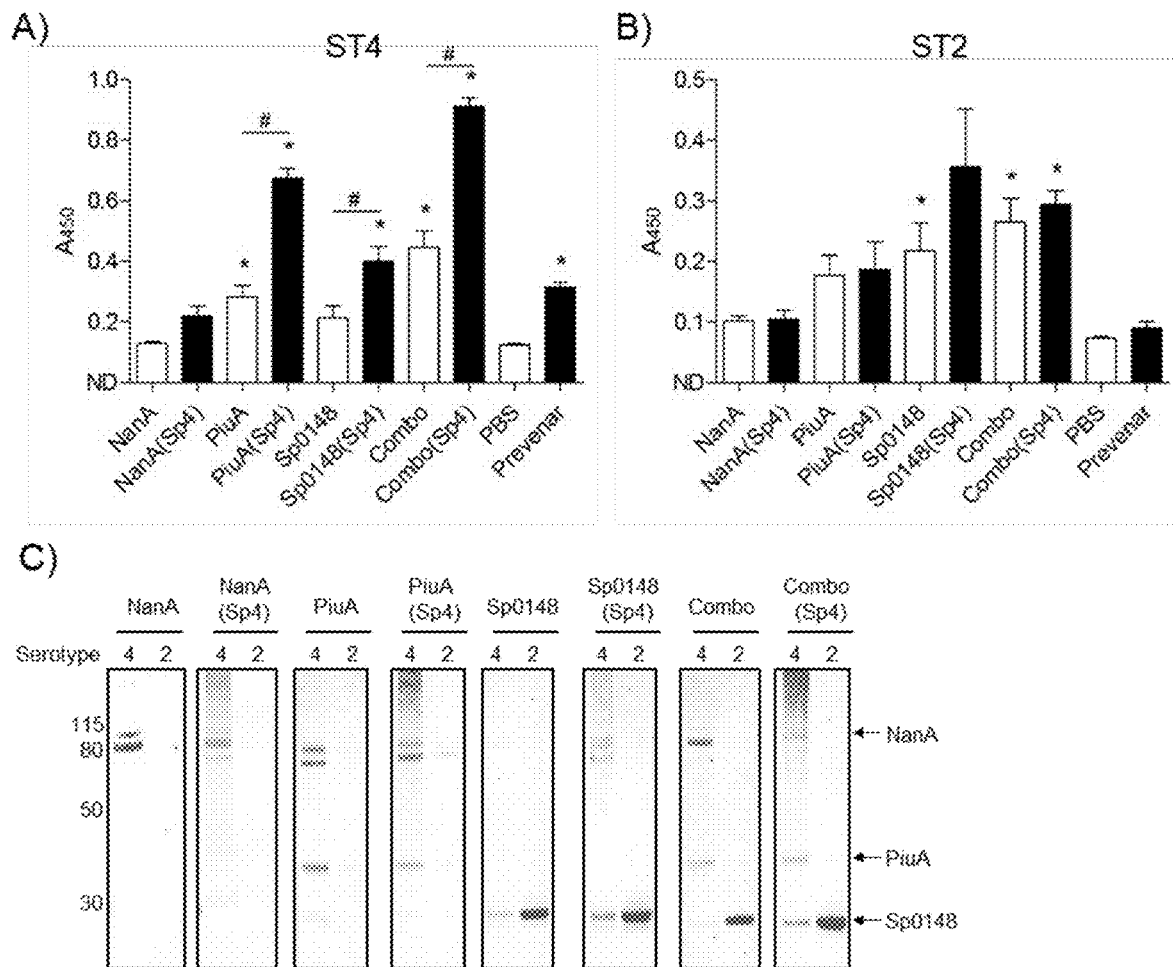
FIG. 2 shows that vaccination with recombinant glycoproteins generates antibodies that recognise homologous and heterologous pneumococcal isolates. Anti-ST4 (FIG. 2A) and anti-ST2 (FIG. 2B) antibodies were measured by whole cell ELISA using pooled antiserum from the glycosylated and unglycosylated vaccine groups. Data are displayed as mean±SEM from three separate cultures. *$P<0.05$ vs PBS #$P<0.05$ protein vs glycoprotein One-way ANOVA with Bonferroni's post-test.

2.2 Antibody Recognition of S. pneumoniae in Sera from Mice Vaccinated with Recombinant Glycoconjugates Antibody recognition of S. pneumoniae in sera from vaccinated mice was assessed using whole cell ELISAs and plates coated with the homologous S. pneumoniae serotype 4 TIGR4 and heterologous serotype 2 D39 strains (FIG. 2A-B). Sera from mice vaccinated with glycoconjugates recognised TIGR4 with a similar ELISA titre, for the Sp0148 group and higher titres for the PiuA or combined three protein glycoconjugates, as sera from mice vaccinated with Prevnar 13 (FIG. 2A). Mice vaccinated with the NanA glycoconjugate generated a non-significant increase in anti-TIGR4 titres. Significant antibody titres were also generated against TIGR4 in serum from mice vaccinated with the unglycosylated PiuA and the combination of all three proteins. As expected, the titres for the D39 whole cell ELISAs did not differ for sera recovered from mice vaccinated with the glycoconjugates or the corresponding proteins, with significant increases in antibody titre seen with mice vaccinated with Sp0148 or the combination of all three proteins (FIG. 2B). Recognition of natural pneumococcal antigens was confirmed by immunoblotting S. pneumoniae lysates with sera from mice vaccinated with the different PGCT glycoconjugates and their cognate proteins (FIG. 2C). Recognition of the three proteins selected for study was confirmed in TIGR4 lysates, as well as recognition of the type 4 pneumococcal capsule in the samples probed with glycoconjugate antiserum. Consistent with the results of the anti-capsule ELISAs (FIG. 2A), the different protein-glycan conjugates gave variable levels of reactivity with the serotype 4 capsule, with the strongest signal occurring with sera from mice vaccinated with the PiuA(Sp4) and Combo(Sp4) glycoconjugates. Consistent with the results of the whole cell ELISAs, the lipoproteins Sp0148 and PiuA were also identified when D39 lysates were probed with sera from vaccinated mice, although the PiuA signal was close to the limit of detection. Together these data indicate that vaccination with the glycoconjugate molecules generated antibodies that recognise both anti-capsular and anti-protein antigen and therefore homologous and heterologous *S. pneumoniae* isolates.

2.3 Vaccination with Recombinant Glycoconjugates Stimulates the Production of Antibodies that are Able to Opsonise Live *S. pneumoniae*

Figure 3:
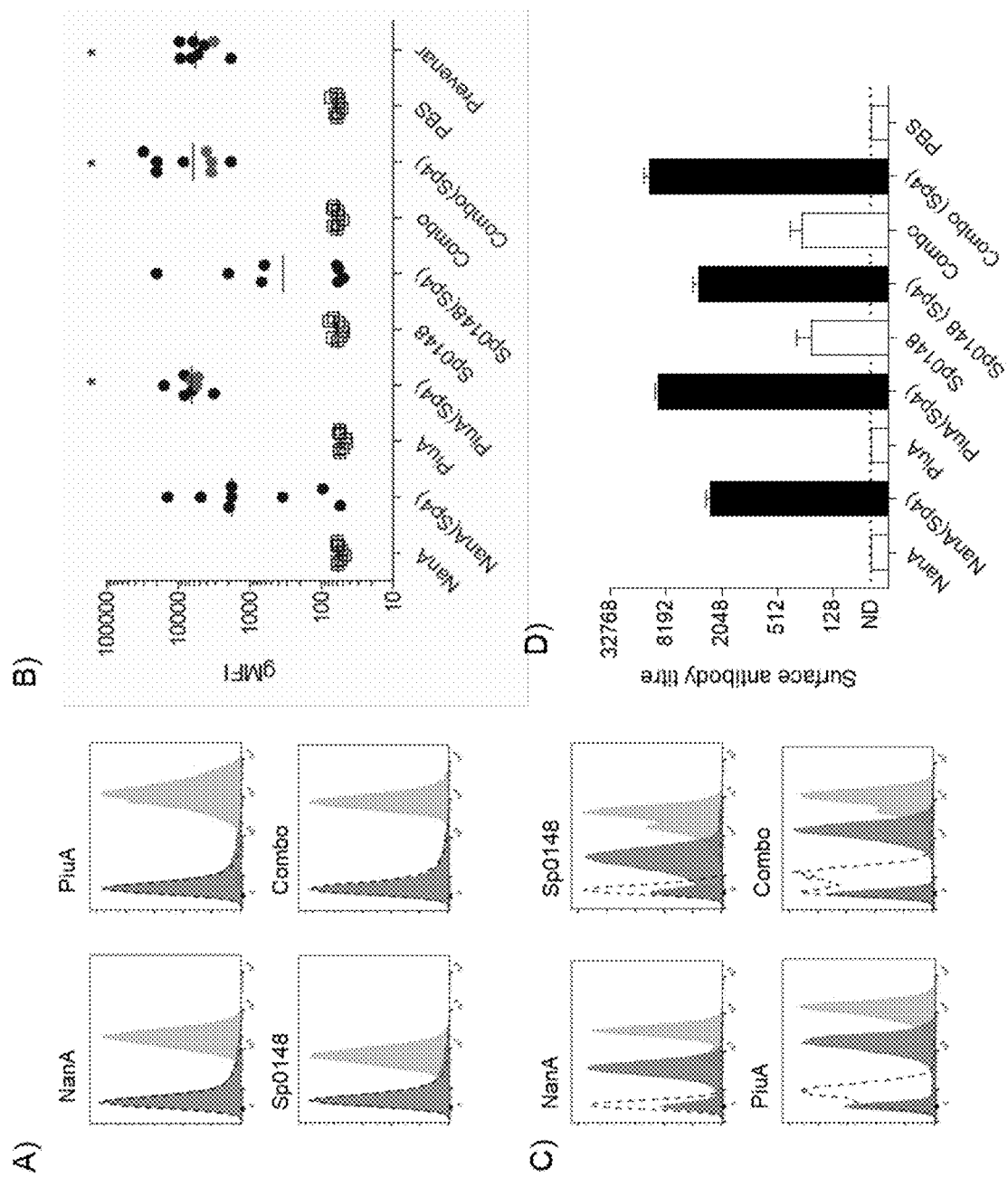
FIG. 3 shows flow cytometry analysis of antibody deposition on streptococcal species.

Flow cytometry assays were used to assess whether vaccination with PGCT glycoconjugates can lead to antibody recognition of live whole *S. pneumoniae*. To specifically investigate anti-capsular recognition, sera from the vaccinated groups were used to assess IgG binding to a *Streptococcus mitis* mutant expressing the *S. pneumoniae* serotype 4 capsule (*S. mitis* (SpT4)) (36). No recognition of wild type *S. mitis* was detected, but *S. mitis* (SpT4) was recognised by individual sera from all groups selected for study (FIG. 3A-B). The degree of IgG binding varied between vaccine groups, with sera from only four and six mice recognising *S. mitis* (SpT4) in the Sp0148 and NanA (Sp4) vaccinated groups respectively, whereas sera from all eight mice vaccinated with the PiuA glycoconjugate or all three protein glycoconjugates caused significant IG binding to *S. mitis* (SpT4) (FIG. 3B). For these two groups the level of antibody binding was comparable to that achieved for the Prevnar-13 vaccinated group. No antibody deposition on the *S. mitis* (SpT4) strain was seen in sera from mice vaccinated with any of the unglycosylated protein antigens, confirming a lack of cross reactivity between the pneumococcal carrier proteins and the *S. mitis* cell surface. These data support the ELISA results that while each of the novel glycoconjugates selected for study can stimulate an anti-Sp4 capsule immune response, a more robust response was stimulated by the PiuA glycoconjugate than the NanA and Sp0148 glycoconjugates.

Flow cytometry IgG binding assays were repeated using the TIGR4 strain. Incubation of TIGR4 with descending dilutions of pooled murine antiserum from the glycoconjugate vaccinated mice groups demonstrated dose dependent IgG binding (FIG. 3C). Comparison of the gMFI readings to a standard curve generated using antiserum from Prevnar-13 vaccinated mice revealed high surface antibody titres in the reactions incubated with serum from mice vaccinated with the four glycoconjugates (FIG. 3D). In addition, in sera from mice vaccinated with the unglycosylated Sp0148 or combination of all three proteins there were detectable levels of surface IgG binding (FIG. 3D). Surface deposition of IgG were no different to the negative control in sera obtained from NanA or PiuA unglycosylated antigens. To assess recognition of the individual protein antigens independent of antibody recognition of the capsule, IgG binding to *S. pneumoniae* with other capsular serotypes was assessed using a fixed concentration of pooled antiserum from mice vaccinated with each glycoconjugate. IgG recognition of non-serotype 4 strains in sera from vaccinated mice was generally weaker than for the TIGR4 strain, and varied between strains (FIG. 4A-D). While there was good levels of IgG binding to the serotype 23F strain, and reasonable levels to the serotype 2 strain, there was little binding to the 6B strain. The ability of different antigens to promote IgG binding varied between strains, with for example NanA inducing the weakest responses for the serotype 23F strain and Sp0148 for the TIGR4 strain, perhaps reflecting differences between the expression level and surface accessibility of individual protein antigens.

Figure 4:
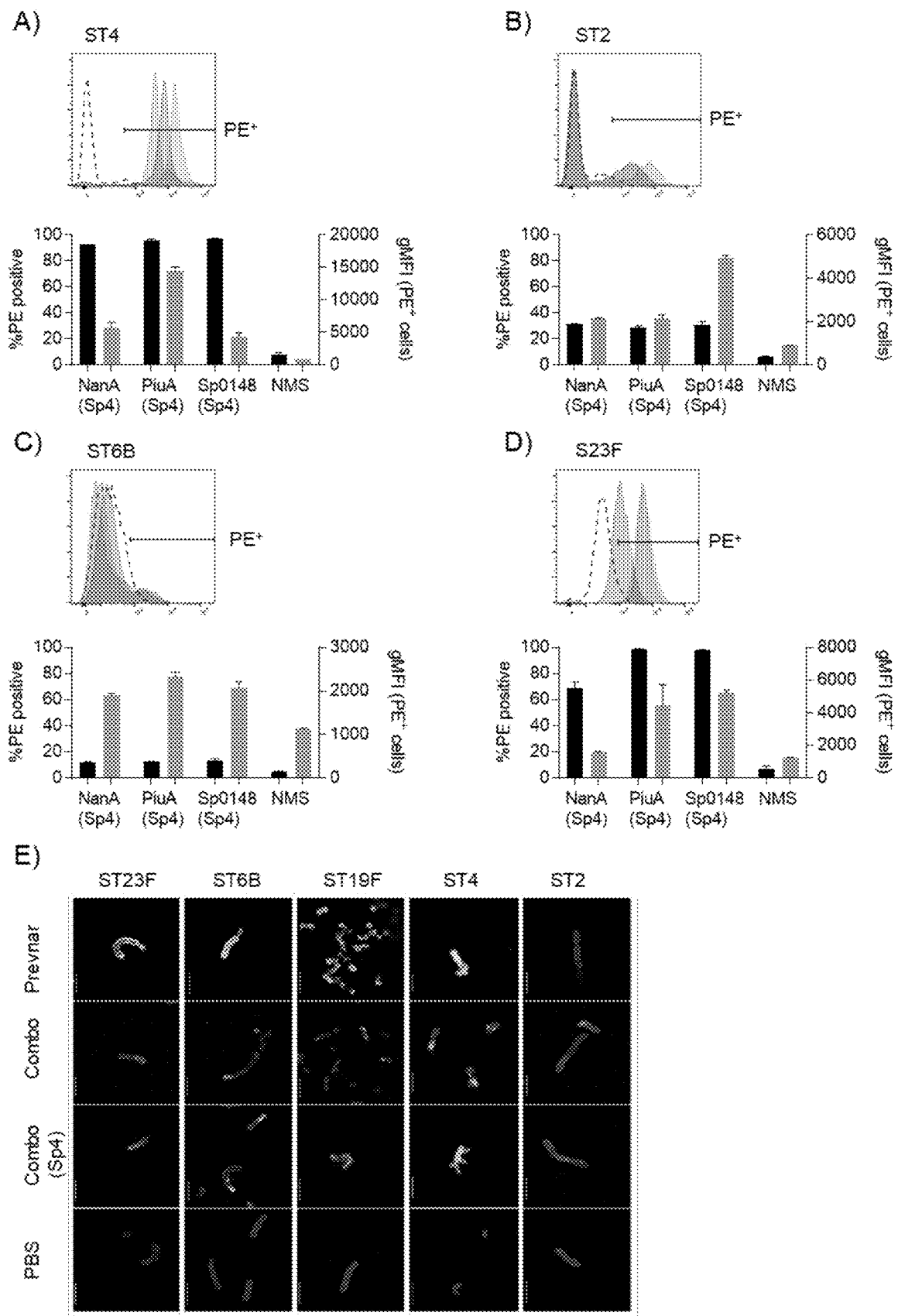
FIG. 4 shows antibody deposition on non-serotype 4 pneumococci.

2.4 Visualisation of Antibody Binding to *S. pneumoniae* in Sera from PGCT Glycoconjugate Vaccinated Mice Recognition of homologous and heterologous pneumococcal isolates was further investigated by fluorescence microscopy using antiserum from the combination vaccine groups and fluorescently labelled anti-mouse secondary antibodies (FIG. 4E). Incubation of the TIGR4 strain in sera from mice vaccinated with all three PGCT glycoconjugates resulted in bright, uniform surface staining across the bacterial cell similar to the results seen for sera from Prevnar-13 vaccinated mice, confirming a high level of IgG binding to the homologous serotype. In contrast, and in keeping with the flow cytometry data, fluorescent staining of the non-serotype strains in sera from PGCT glycoconjugated vaccinated mice was weaker, patchy, and more variable between strains. However, stained cocci were visible in all serotypes when sera from mice vaccinated with either a glycosylated or unglycosylated mix of all three protein antigens, including the serotype 2 strain that is not recognised by sera from Prevnar-13 vaccinated mice. Together the ELISA, flow cytometry and immunofluorescence data demonstrate that PGCT glycoconjugates can induce anti-capsular IgG responses that vary in strength between carrier proteins but which can be similar in strength (e.g. PiuA glycoconjugates) to that achieved after vaccination with Prevnar-13. In addition, the PGCT glycoconjugates stimulate significant antibody responses to protein antigens that can opsonise the heterologous *S. pneumoniae* serotypes and which potentially provide protection against multiple *S. pneumoniae* strains.

Figure 5:
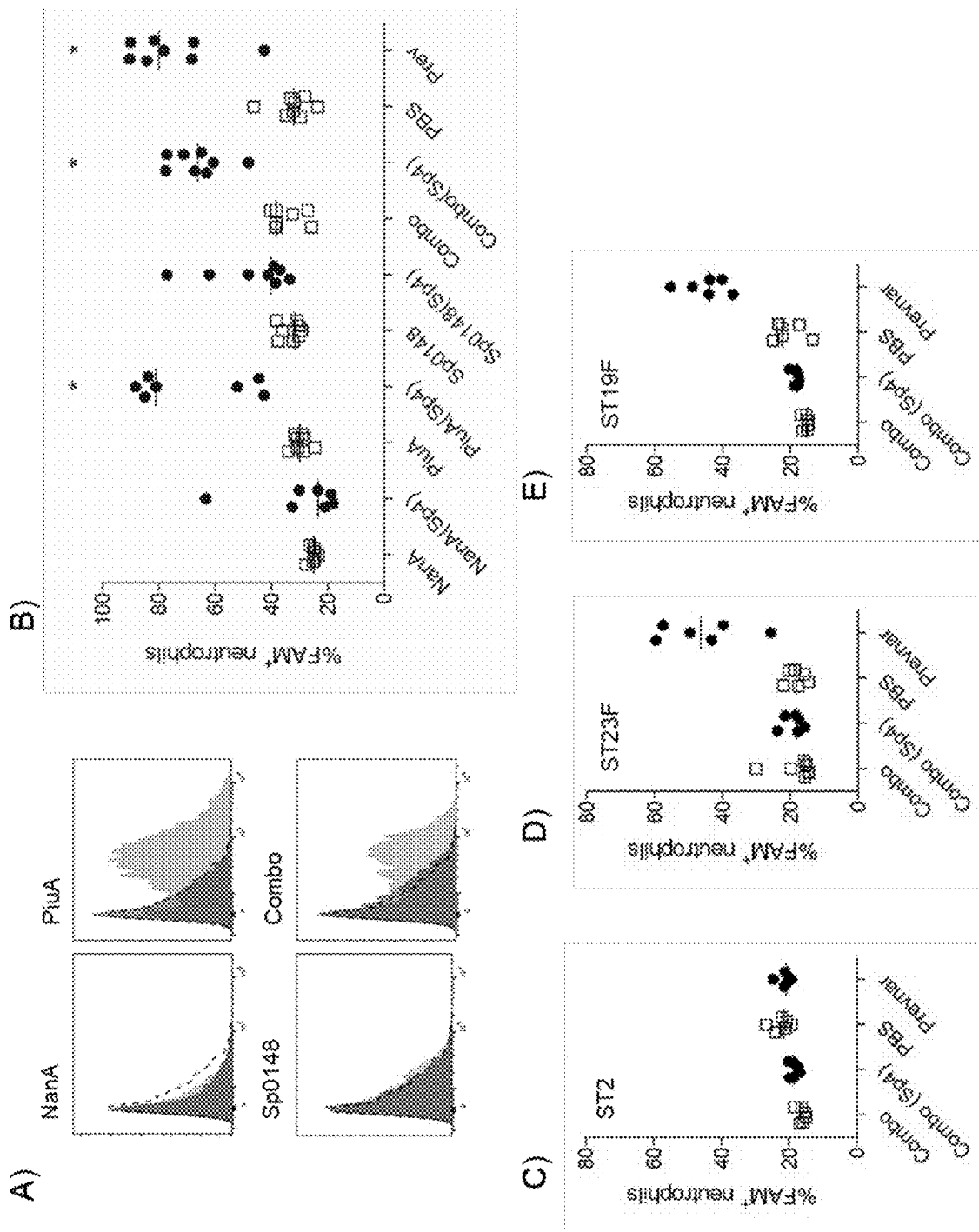
FIG. 5 shows the effect of antiserum samples on interaction of S. pneumoniae with human neutrophils.

2.5 Protective Efficacy of Vaccination of Mice with Recombinant Glycoconjugates Produced by PGCT To determine if the density of antibody deposition on TIGR4 was sufficient to promote opsonophagocytosis, neutrophil uptake assays were performed using freshly isolated human neutrophils (37). Incubation in sera from mice vaccinated with the PiuA(Sp4) glycoconjugate or a combination of glycoconjugates from all three proteins both promoted neutrophil uptake of the TIGR4 *S. pneumoniae* strain, indicating that a functional anti-capsular humoral immune response was being generated in response to recombinant type 4 capsular antigen made using PGCT (FIG. 5A). However, sera from mice vaccinated with the Sp0148 (Sp4), NanA(Sp4) or the unglycosylated proteins (individually or in combination) failed to promote neutrophil phagocytosis in this assay (FIG. 5B). The combination conjugates also failed to promote neutrophil phagocytosis for non-serotype 4 strains tested (FIG. 5C-E)

Figure 6:
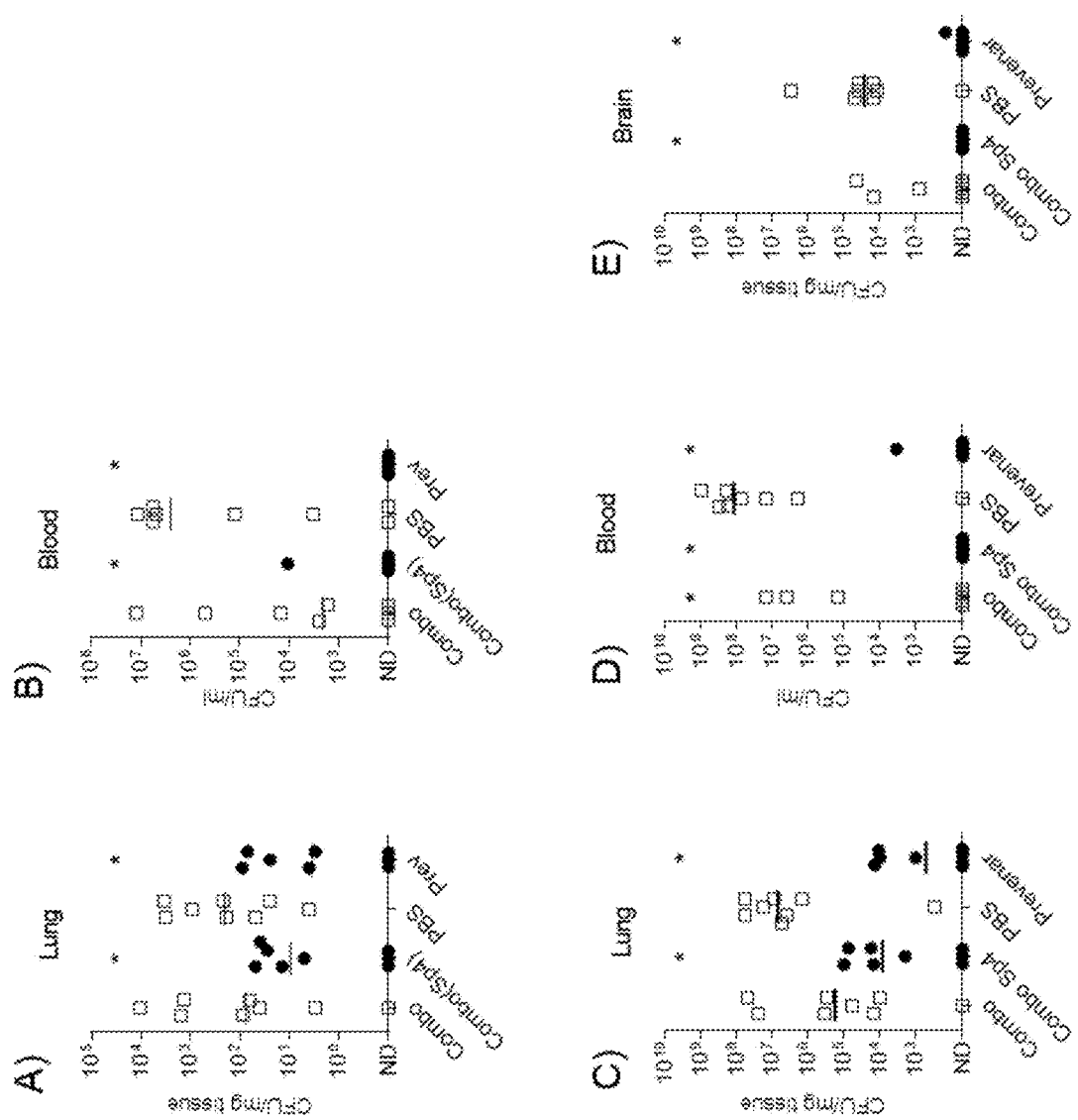
FIG. 6 shows that vaccination with recombinant glycoconjugates provides homologous but not heterologous protection against pneumococcal pneumonia. Mice were vaccinated with the glycosylated and unglycosylated combination vaccines and challenged intranasally with $1\times10^7$ CFU of TIGR4 for 48 h (7A-B) or Serotype 4 (7C-E). Bacterial burdens were determined by serial dilution and plating. *$p<0.05$ Kruskal-Wallis with Dunn's post-test (vs PBS).

Mouse models of infection were used to assess the protective efficacy of glycoconjugates made using PGCT. Mice were vaccinated with Prevnar, or a combination of all three PGCT glycoconjugates or of the unglycosylated proteins, and then challenged by intranasal inoculation of the TIGR4 strain (pneumonia with sepsis model) or the serotype 4 strain, which is known to cause meningitis. After 48 hours, mice were culled and the level of infection assessed using target organ CFU. In the TIGR4 challenge model, vaccination with the three PGCT glycoconjugates in combination almost completely prevented septicaemia and resulted in an approximately $\log_{10}$ reduction in lung CFU, a very similar level of protection to that provided by vaccination with Prevnar-13 (FIG. 6A-B). Although not statistically significant, there was also a reduction in median CFU/ml recovered from the blood in mice vaccinated with the combination of the unglycosylated proteins alone. In the meningitis model, vaccination with the three PGCT glycoconjugates in combination completely prevented septicaemia and meningitis, and resulted in an approximately 3 $\log_{10}$ reduction in lung CFU (FIG. 6C-E). Again, this was a very similar level of protection to that provided by vaccination with Prevnar-13. For mice vaccinated with the combination of the unglycosylated proteins alone, median blood, lung and brain CFU were all lower than results for the negative control although only the blood data were statistically significant. The data from these mouse models demonstrate that a S. pneumoniae capsular and protein antigen made using PGCT can be highly protective against infection with the homologous S. pneumoniae serotype, providing a level of protection as good as vaccination with an existing commercial PCV preparation. Furthermore, the protein components also generated a protective response independent of capsular antigen, suggesting a PGCT vaccine will be able to provide cross-serotype protection.

In the experiments above, protein glycan coupling technology is used to produce a low cost multicomponent, glycoconjugate vaccine that incorporates three surface antigens glycosylated with recombinant serotype 4 capsule. The findings include: (a) a S. pneumoniae glycoconjugate made using PGCT is as immunogenic as a commercial PCV and offers a similar level of protection in mouse models of pneumonia and meningitis; (b) a S. pneumoniae protein antigen can be used as a carrier protein for a PCV vaccine instead of one of the established conjugate vaccine carrier proteins; (c) the anti-capsular immunogenicity of a glycoconjugate made using PGCT varies markedly with the carrier protein; (d) the carrier proteins are immunogenic, stimulating an antibody response that is able to offer some degree of protection against meningitis and sepsis independent of capsular antibody. The data demonstrate that PGCT may provide an alternative methodology for manufacturing PCV that is cheaper than existing chemical conjugation methodologies and generates a similar level of serotype-specific protection that can be used in the developing world to prevent severe S. pneumoniae infections including meningitis. In addition, PGCT could make a PCV that includes a range of S. pneumoniae protein carrier proteins and thereby provide at least some degree of serotype-independent immunity.

A major finding from our data that has wide implications for vaccine development is the identification of additional carrier proteins that promote antibody responses to capsular antigens. At present only four proteins have been used for making glycoconjugates, but our data show that PiuA would be an additional option. The other two proteins used to make glycoconjugates, Sp_0148 and NanA, were considerably less effective at generating anti-glycan responses than PiuA. Indeed, it is conceivable that most of the anti-capsule response generated by the combination vaccine resulted from the presence of glycosylated PiuA. The reasons why there were such marked differences in the efficacy of the carrier protein in promoting anti-capsular antibody is not clear. Immunoblots suggested that this is not simply due to a greater quantity of PiuA glycoconjugate, as in fact the NanA glycoconjugate seemed to be the most abundant. The choice of carrier protein and site of glycosylation is important for the generation of a robust anti-capsule IgG response, and recent data suggest glycoconjugates generate an antibody response to glycan by presentation of a glycosylated epitope bound to MHCII directly to the T cell receptor (21, 22). This mechanism would explain our data, as the strength of the anti-capsular antibody responses will be affected by the choice of carrier protein, and perhaps by the site of covalent linkage to capsular antigen. These data suggest that screening additional S. pneumoniae proteins should identify additional carrier proteins for glycoconjugate vaccines that are able to result in strong antibody responses to capsular or other glycan antigens.

The major advantage of using S. pneumoniae protein antigens as carrier proteins for a PCV made using PGCT is that these proteins can induce an additional immune response that can be protective. This immune response to protein antigens could also include T cell mediated immunity including TH17 responses (24, 40) which could theoretically enhance mucosal immunity compared to pure antibody responses. We investigated whether a combination glycoconjugate produced using PGCT incorporating the type 4 pneumococcal capsule conjugated to three conserved S. pneumoniae protein antigens, the endothelial cell invasin NanA (29), the Th17 stimulating antigen Sp0148 (24) and the ABC transporter PiuA (34), could stimulate homologous and heterologous immunity against S. pneumoniae. Our data confirm that vaccination with the carrier proteins was able to generate a good antibody response that could recognise different strains of live S. pneumoniae. Vaccination with these proteins alone reduced bacterial CFU present in blood and meninges after challenge with S. pneumoniae, confirming the protective potential of antibody responses to the carrier protein component. However, despite selecting a known Th17 inducing antigen (SP_0148) vaccination with the proteins alone did not prevent infection at the lung level and the level of protection against systemic infection was weaker than that provided by anticapsular responses. Furthermore, the antibody responses to the three proteins differed in their ability to recognise different S. pneumoniae strains.

In summary, the data presented here demonstrate that PGCT can make a S. pneumoniae glycoconjugate that is as efficacious as an existing commercial PCV in preventing serotype specific infection but in addition can stimulate protective immunity against heterologous serotypes.

TABLE 1

| Species | Strain | Description |
| --- | --- | --- |
| E. coli | W3110 | K12 derivative |
| E. coli | W311B | W3110 derivative containing chromosomally inserted oligosaccharyltransferase PglB |
| E. coli | W3110 pB4-4 | W3110 containing Spn. type 4 capsule operon |

TABLE 1-continued

| Species | Strain | Description |
|---|---|---|
| E. coli | W311B pB4-4 | W311B containing Spn. type 4 capsule operon |
| E. coli | W3110 pEXT21 (NanA)* | recombinant NanA production |
| E. coli | W3110 pEXT21 (PiuA)* | recombinant PiuA production |
| E. coli | W3110 pEXT21 (Sp0148)* | recombinant Sp0148 production |
| E. coli | W311B pB4-4 pEXT21 (NanA) | glycosylated NanA production |
| E. coli | W311B pB4-4 pEXT21 (PiuA) | glycosylated PiuA production |
| E. coli | W311B pB4-4 pEXT21 (Sp0148) | glycosylated Sp0148 production |
| E. coli | W311B pB4-4 pEXT20 | Enhanced Sp4 glycosylation |
| E. coli | W311B pB4-4 pEXT21 (NanA) pEXT20 | glycosylated NanA production |
| E. coli | W311B pB4-4 pEXT21 (PiuA) pEXT20 | glycosylated PiuA production |
| E. coli | W311B pB4-4 pEXT21 (Sp0148) PEXT20 | glycosylated Sp0148 production |
| E. coli | W3110 pB4-4 pEXT21 (PiuA) pEXT20 | recombinant PiuA/LLO production |
| S. pneumoniae | TIGR4 | Serotype 4 |
| S. pneumoniae | D39 | Serotype 2 |
| S. pneumoniae | EF3030 | Serotype 19F |
| S. pneumoniae | 6B | Serotype 6B |
| S. pneumoniae | 23F | Serotype 23F |
| S. mitis | | S. mitis expressing WT capsule |
| S. mitis | | S. mitis expressing Spn. type 4 capsule |

*Used for vaccine production

REFERENCES

1. Jacobs D M Yung F, Hart E, Nguyen M N H, Shaver A. Trends in pneumococcal meningitis hospitalizations following the introduction of the 13-valent pneumococcal conjugate vaccine in the United States. Vaccine. 2017; 35(45):6160-5.
2. Polkowska A, et al BMJ Open. 2017; 7(5):e015080.
3. Hsu H E, Shutt K A, Moore M R, Beall B W, Bennett N M, Craig A S, et al. Effect of pneumococcal conjugate vaccine on pneumococcal meningitis. N Engl J Med. 2009; 360(3):244-56.
4. Bijlsma M W, Brouwer M C, Kasanmoentalib E S, Kloek A T, Lucas M J, Tanck M W, et al. Community-acquired bacterial meningitis in adults in the Netherlands, 2006-14: a prospective cohort study. Lancet Infect Dis. 2016; 16(3):339-47.
5. Alari A, Chaussade H, Domenech De Celles M, Le Fouler L, Varon E, Opatowski L, et al. Impact of pneumococcal conjugate vaccines on pneumococcal meningitis cases in France between 2001 and 2014: a time series analysis. BMC medicine. 2016; 14(1):211.
6. Pirez M C, Mota M I, Giachetto G, Sanchez Varela M, Galazka J, Gutierrez S, et al. Pneumococcal Meningitis Before and After Universal Vaccination With Pneumococcal Conjugate Vaccines 7/13, Impact on Pediatric Hospitalization in Public and Nonpublic Institutions, in Uruguay. Pediatr Infect Dis J. 2017; 36(10):1000-1.
7. Nhantumbo A A, Weldegebriel G, Katsande R, de Gouveia L, Come C E, Cuco A Z, et al. Surveillance of impact of PCV-10 vaccine on pneumococcal meningitis in Mozambique, 2013-2015. PLoS One. 2017; 12(6): e0177746.
8. Azevedo J, Dos Anjos E S, Cordeiro S M, Dos Santos M S, Escobar E C, Lobo P R, et al. Genetic profiles and antimicrobial resistance of Streptococcus pneumoniae non-PCV10 serotype isolates recovered from meningitis cases in Salvador, Brazil. J Med Microbiol. 2016; 65(10): 1164-70.
9. Hausdorff W P, Bryant J, Paradiso P R, Siber G R. Which pneumococcal serogroups cause the most invasive disease: implications for conjugate vaccine formulation and use, part I. Clin Infect Dis. 2000; 30(1):100-21.
10. Geno K A, Gilbert G L, Song J Y, Skovsted I C, Klugman K P, Jones C, et al. Pneumococcal Capsules and Their Types: Past, Present, and Future. Clin Microbiol Rev. 2015; 28(3):871-99.
11. Skov Sorensen U B, Yao K, Yang Y, Tettelin H, Kilian M. Capsular Polysaccharide Expression in Commensal Streptococcus Species: Genetic and Antigenic Similarities to Streptococcus pneumoniae. MBio. 2016; 7(6).
12. Miller E, Andrews N J, Waight P A, Slack M P, George R C. Herd immunity and serotype replacement 4 years after seven-valent pneumococcal conjugate vaccination in England and Wales: an observational cohort study. Lancet Infect Dis. 2011; 11(10):760-8.
13. Waight P A, Andrews N J, Ladhani S N, Sheppard C L, Slack M P, Miller E. Effect of the 13-valent pneumococcal conjugate vaccine on invasive pneumococcal disease in England and Wales 4 years after its introduction: an observational cohort study. Lancet Infect Dis. 2015; 15(5):535-43.
14. Bonten M J, Huijts S M, Bolkenbaas M, Webber C, Patterson S, Gault S, et al. Polysaccharide conjugate vaccine against pneumococcal pneumonia in adults. N Engl J Med. 2015; 372(12):1114-25.
15. van Hoek A J, Miller E. Cost-Effectiveness of Vaccinating Immunocompetent >/=65 Year Olds with the 13-Valent Pneumococcal Conjugate Vaccine in England. PLoS One. 2016; 11(2):e0149540.
16. Wacker M, Linton D, Hitchen P G, Nita-Lazar M, Haslam S M, North S J, et al. N-linked glycosylation in Campylobacter jejuni and its functional transfer into E. coli. Science. 2002; 298(5599):1790-3.
17. Kay E J, Yates L E, Terra V S, Cuccui J, Wren B W. Recombinant expression of Streptococcus pneumoniae capsular polysaccharides in Escherichia coli. Open Biol. 2016; 6(4):150243.
18. Linton D, Dorrell N, Hitchen P G, Amber S, Karlyshev A V, Morris H R, et al. Functional analysis of the Campylobacter jejuni N-linked protein glycosylation pathway. Mol Microbiol. 2005; 55(6):1695-703.

19. Donnelly J J, Deck R R, Liu M A. Immunogenicity of a *Haemophilus influenzae* polysaccharide-*Neisseria meningitidis* outer membrane protein complex conjugate vaccine. J Immunol. 1990; 145(9):3071-9.
20. Forsgren A, Riesbeck K, Janson H. Protein D of *Haemophilus influenzae*: a protective nontypeable *H. influenzae* antigen and a carrier for pneumococcal conjugate vaccines. Clin Infect Dis. 2008; 46(5):726-31.
21. Avci F Y, Li X, Tsuji M, Kasper D L. A mechanism for glycoconjugate vaccine activation of the adaptive immune system and its implications for vaccine design. Nat Med. 2011; 17(12):1602-9.
22. Stefanetti G, Hu Q Y, Usera A, Robinson Z, Allan M, Singh A, et al. Sugar-Protein Connectivity Impacts on the Immunogenicity of Site-Selective *Salmonella* O-Antigen Glycoconjugate Vaccines. Angew Chem Int Ed Engl. 2015; 54(45):13198-203.
23. Genschmer K R, Accavitti-Loper M A, Briles D E. A modified surface killing assay (MSKA) as a functional in vitro assay for identifying protective antibodies against pneumococcal surface protein A (PspA). Vaccine. 2013; 32(1):39-47.
24. Moffitt K L, Gierahn T M, Lu Y J, Gouveia P, Alderson M, Flechtner J B, et al. T(H)17-based vaccine design for prevention of *Streptococcus pneumoniae* colonization. Cell Host Microbe. 2011; 9(2):158-65.
25. Malley R, Trzcinski K, Srivastava A, Thompson C M, Anderson P W, Lipsitch M. CD4+ T cells mediate antibody-independent acquired immunity to pneumococcal colonization. Proc Natl Acad Sci USA. 2005; 102(13): 4848-53.
26. Tu A H, Fulgham R L, McCrory M A, Briles D E, Szalai A J. Pneumococcal surface protein A inhibits complement activation by *Streptococcus pneumoniae*. Infect Immun. 1999; 67(9):4720-4.
27. Cheng Q, Finkel D, Hostetter M K. Novel purification scheme and functions for a C3-binding protein from *Streptococcus pneumoniae*. Biochemistry. 2000; 39(18): 5450-7.
28. Janulczyk R, Iannelli F, Sjoholm A G, Pozzi G, Bjorck L. Hic, a novel surface protein of *Streptococcus pneumoniae* that interferes with complement function. J Biol Chem. 2000; 275(47):37257-63.
29. Uchiyama S, Carlin A F, Khosravi A, Weiman S, Banerjee A, Quach D, et al. The surface-anchored NanA protein promotes pneumococcal brain endothelial cell invasion. J Exp Med. 2009; 206(9):1845-52.
30. Yamaguchi M, Nakata M, Sumioka R, Hirose Y, Wada S, Akeda Y, et al. Zinc metalloproteinase ZmpC suppresses experimental pneumococcal meningitis by inhibiting bacterial invasion of central nervous systems. Virulence. 2017:1-9.
31. Mahdi L K, Wang H, Van der Hoek M B, Paton J C, Ogunniyi A D. Identification of a novel pneumococcal vaccine antigen preferentially expressed during meningitis in mice. J Clin Invest. 2012; 122(6):2208-20.
32. Cuccui J, Thomas R M, Moule M G, D'Elia R V, Laws T R, Mills D C, et al. Exploitation of bacterial N-linked glycosylation to develop a novel recombinant glycoconjugate vaccine against *Francisella tularensis*. Open Biol. 2013; 3(5):130002.
33. Riddle M S, Kaminski R W, Di Paolo C, Porter C K, Gutierrez R L, Clarkson K A, et al. Safety and Immunogenicity of a Candidate Bioconjugate Vaccine against *Shigella flexneri* 2a Administered to Healthy Adults: a Single-Blind, Randomized Phase I Study. Clin Vaccine Immunol. 2016; 23(12):908-17.
34. Brown J S, Ogunniyi A D, Woodrow M C, Holden D W, Paton J C. Immunization with components of two iron uptake ABC transporters protects mice against systemic *Streptococcus pneumoniae* infection. Infect Immun. 2001; 69(11):6702-6.
35. Bernatchez S, Szymanski C M, Ishiyama N, Li J, Jarrell H C, Lau P C, et al. A single bifunctional UDP-GlcNAc/Glc 4-epimerase supports the synthesis of three cell surface glycoconjugates in *Campylobacter jejuni*. J Biol Chem. 2005; 280(6):4792-802.
36. Wilson R, Cohen J M, Reglinski M, Jose R J, Chan W Y, Marshall H, et al. Naturally Acquired Human Immunity to Pneumococcus Is Dependent on Antibody to Protein Antigens. PLoS Pathog. 2017; 13(1):e1006137.
37. Reglinski M, Gierula M, Lynskey N N, Edwards R J, Sriskandan S. Identification of the *Streptococcus pyogenes* surface antigens recognised by pooled human immunoglobulin. Sci Rep. 2015; 5:15825.
38. Gessner B D, Mueller J E, Yaro S. African meningitis belt pneumococcal disease epidemiology indicates a need for an effective serotype 1 containing vaccine, including for older children and adults. BMC Infect Dis. 2010; 10:22.
39. Wacker M, Feldman M F, Callewaert N, Kowarik M, Clarke B R, Pohl N L, et al. Substrate specificity of bacterial oligosaccharyltransferase suggests a common transfer mechanism for the bacterial and eukaryotic systems. Proc Natl Acad Sci USA. 2006; 103(18):7088-93.
40. Zhang Z, Clarke T B, Weiser J N. Cellular effectors mediating Th17-dependent clearance of pneumococcal colonization in mice. J Clin Invest. 2009; 119(7):1899-909.
41. Terra et al (2012) J. Med. Microbiol. 61 919-926.
42. WO2009/104074
43. WO2014/114926

| sequences |
|---|
| GGATCCGAATTCCATTTTAAATAAGGAGGAATAACATAATGAAAAAGATTTGGCTGGCGCTGGCGCTGGTTTAGTTTTAGCGTTTAGCGCATCGGCGGCGCAGGGAGGCGATCAGA<br>ACGCGACCGGTTGGCGCCGCCCAGTGGCCCAGTGGCTTCCTTCTGCTTCTGAAAAGTTCCTGAAAAGTTCTGAAAAGTTGTGACCTTTGACCTTGACCTTGACCGATACTATTCGCGTTCGCGGACCCTCGCTCGGCCTCGGCCTCGGCGGCCCTTGACCCTTGAGCCTGAT<br>GAATGCTACAAGCTGTTCCGACTTATCTAGAAAAGACTAGTGGAACTGTCAAAAATGTGGTTCTAAAGACTTGGAACTGTTCAAAAATGTGGTTCTATGAAGACTATCGCCGCCTTGAGCCTGAT<br>TGATTATCGCTTCGCCACGTACACAGAAAATCGTAGACAAATTCAAAGAAATCGCCCACGTTCTCTTCCAAGCAGACATCCAAGCAGACATCGTATTAGAAGCGAAGTCGTATTGAAGCGACTTCTACAAGGCTAATA<br>TCGAATCCTTAGCAAGTGCCTTCGGCGACAAATGGCAAGACAGAAAAGCCAAGACAGAAAAGCAAGAGATTGCAAGAGATTGCAGCCATCCAAGAAGTCGCTACTAAAATGAAAGCTCGACA<br>AAAAAGCCCTTGCGATCCTCCTTAATGAAGCAAGAAGTCAGCTTTGAAAGTGTCAAAGAAATCAACCTGACAAATCAACCTGACTGACCCTTGCCATGGTGGGACAACTCTAGCAACG<br>ACGGTGTCCTAGAAAATGCCCTTATCGCTGCTAAAAATGGTAAGATTATCCACCTAGATTATCCACCAGACCTCTGGTATCTAAGCGACGGACCGACTTGAATCAACAA<br>AACTCATGATTGAAGACATACAAAAGCTTTGAAAGGAGGCGATCAGAACCGCAGAACCGCAGGATCCATCACCATCACCATCACCATCATTAAGTCTAGAGGATCC |

SEQ ID NO: 1 (PiuA coding sequence) with sequons (dashed underline),

MKKIWLALAG LVILAFSASAA QGGDQNATGG ALVASFLLLL GACSTNSSTS QTETSSSAPT EVTIKSSLDE VKLSKVPEKI VTFDLGAADT
IRALGFEKNI VGMPTKTVPT YLKDLVGTVK DKSIQEVATK QKAKEELTKL LASAFGETGT QKAKEELTKL VLFQASKDDY WTSTKANIES
LASAFGETGT QKAKEELTKL NESSDKKALA ILLNEGKMAA FGAKSRFSFL YQTLKFKPTD TKFEDSRHGQ EVSFESVKEI
NPDILFVINR TLAIGGDNSS NDGVLENALI AETPAAKNGK IIQLTPDLWY LSGGGLESTK LMIEDIQKAL KGGDQNATGG HHHHHHHH
SEQ ID NO: 2 PiuA amino acid sequence with sequons (solid underline), His tag (italics) and leader peptide
(dotted underline).

ALVASFLLLL GACSTNSSTS QTETSSSAPT EVTIKSSLDE VKLSKVPEKI VTFDLGAADT IRALGFEKNI VGMPTKTVPT YLKDLVGTVK
NVGSMKEPDL EAIAALEPDL ALVASFLLLL GACSTNSSTS VLFQASKDDY WTSTKANIES LASAFGETGT QKAKEELTKL
NESSDKKALA ILLNEGKMAA FGAKSRFSFL YQTLKFKPTD TKFEDSRHGQ EVSFESVKEI NPDILFVINR TLAIGGDNSS NDGVLENALI
AETPAAKNGK IIQLTPDLWY LSGGGLESTK LMIEDIQKAL K
SEQ ID NO: 3 (PiuA amino acid sequence)

| |
|---|
| GGATCCGAATTCCATTTTAAATAAGGAGGAATAACATAATGAAAAAGATTTGGCTGGCGCTGGTGTTTAGTTTTAGCGCTTAGCGCCAGCTTCTTCAGAGACTGAACTTTCTGCA<br>ACGCGACCGGTGGCGCCGCCCAGTGGCCCAGTGGCTCAACCTGACAACCTGACTGATACAGAAAAGACCAGCTTCTTCAGAGACTGAACTTTCTGCA<br>ATAAGCAAGAAGAACAAGAAGATAACGAAGATAACGAAGTTAAGACAATTACTATGGCCAGAGATTTGGAAACAGTTGGAACAGTCGAAACAGTCTGAAACCAGAGATTGAAACCA<br>ATGCTTCAAATCGTCAGAGATTGCAGAGATTGCAGAGATTGCAGAGATTGCAGAGAGATTTGAAACAGTTGGAACAGTCGAAACAGTCCAAGCCCAAGCCAATTCT<br>ATAATCTCCTTTCTCCAGCAGCTTCTCCAGCAGCTTCTCCAGCAGCTTGTCAAGTGTAATATGTAATATGTACCCAGATCATGGGATCATGGGATCATTACA<br>ATAATTACAACGATGCAATGCAGTCCAGTCGCAGTTCAGTCCAGCAGCAGCCAATAATCTAAGATGCAATTGAAAGATGTAATATCATGTGCGATCCATTGTGCGATCCCTGGGGT<br>ACGGGTATTATCGAAGGTATTATCGAAGGTTTCCACTACTCACCACCCAGAATCCACCAGAATGGAGATGTACCAACCAGTGGATATAAGATCATATAAGATTAAAACGCTCAGCACTAACGCTGAGCACT<br>CAAATACTAACGATTCGAAATCGATTCGAAATCGATGTTGCCTATATCGTATATCGTAACCATCGAAACTAACCATCGAAGACTGTAAGCGATGAAAGCGATGGAAGACATTGAAGAGATTGAAGAGATAAGGAA<br>GAGCGGCTTTAACGACAATGACAATGACAATGACAATGAAAACGGAACGGAATGAAAACCGGAATGAAAACCGGAATAATGAAAATCACAATCCTCAATCCACTGAATTCAAAACGAACAAAAATGCAATATCTTTAACGAATCAAGAATCAAGAATCAAGAACTCTATCATG<br>ACATGTTCGAGAAGGAAGGGCCAAGAGGGCCATCTGTTTGAAGATGAAAACGGAATGAAAACCGGAATGAAAACCGGAATCCTTGAGACAGTTGAGACAGAAAACAGACGTTGCCAAGCAAGGGAAGGGAATCATATCATATCA<br>CTTATCCAATTCGAGAAATTTCGAGAAATTCGAGAAATTCTCAAGATTCTCTATCATCTCTATCATCTTCAGATCTTCAGATCTTCAGATCAGATCATCATGGAAAACCAGCCTATATAAGGATTAATCATGATCAT<br>AGGGTAACCATCCAGAAATTCCAGAAATGACTGTTCTGATGCTTATCCGATGTACTGATGCTCAGTGCAGTTAAGTCAGGACAGGACAGAAAGCGCAAGGAAGGATCTATACA<br>GGTCAGCGCCTTCAGCAGCTATATACGACGTTTAAACGACGTTTAAACGATCATCCGATTGCAAGCATATCCGATTCATCCAAGAAGAATGGCCAATTAGGAGAAACACCAAGGAGAAACACCAATTGAAATGAAATGAAATGAAATCAAATCATGACAGGACAGGACGATTCGAAATGGAAGGGTCAAGGTCAAGG<br>ATAACCGATAGACGGTCAAAAGATCTGCATGACAGAGATCTCCATGACAGAGAGATCAACAATAGACCGATGAGACCTGGAGCATATACACCGGAGAAACTCATAACCTTGGACACATAGAGCATATACACCGGAGAAACTCATAACCTTTA<br>TGCGTGTGGTTTGACTGGACTGATGTCCTACAAGAACACTGGACTGATGTCACTACAAGATATCATCCAGTTCGATGCAAGTTTGAGAATTAGGTCTGCGGACCGTCAACAAGCATTCACAAAAGGTACGACGTCTATGTTCAAATTCAAATGTCTG<br>CTATCCATACGACGACGACGAAGATAACATCTCAGTATGCAGGATCAGGTGACCGAAGTCCTCCCAAGAATTAGGAGTATGCCATCTTGTATGAACATATACATATGAACATATTGAACATATTGAAGAAATTGATAGTTGATAGAA<br>CTTGGCTCAAACACAAATCCAATTCAAATTGCCTATAATTCGCCTAGAAAAGGAGAGAGTTTGCCTATAATTCGCCTATAATTCGCCTATAATTCGCCTCGAATTAGGAGAAATGGGGAATTAGGAGAGTATGCCATCTTGTATGAACATTTGTATGAACATTTGTATGAACATTGAAGAAATGGGGAATGGGGAATTAGGAGAGTTGAGTAATGGGAATTAGGAGAGTTGAGTGA |

Sequences

CCTATACCCTATCATTTAGAAAATTAATTGGGACTTTTTGAGCAAAGATCTGATTTCTCCTACCGAAGCGAAAGTGAAGCGAACTAGAGAGATGGGCAAGGAGTTATTGGCT
TGGAGTTCGACTCAGAAGTATTGGTCAACAAGGCTTCCAACCCTTCAATTGGCAAATGGTAAAACACCTTCATGACCCAGTATGATGATACAAAACCCTCTATTACAGTGG
ATTCAGAGGATATGGTCAAAAGTTACAGGTTTGCAGAAGGTGCAATTGAAAGTATGCATAATTACCAGTCTCTGTGCGGGCACTAAGCTTTGAATGGAATGAACGGAA
GCGAAGCTGCTGTTCATGAAGTGCCAGAAATACACAGGCCCATTAGGGACATCACAGGCTCCAACAGTCGAAGAAGCCAGAATACACAGGCCACTAGGGACATCCG
GCGAAGAGCCAGCCCCGACGTCGAGAAGCCAGAATACACAGGCCCACTAGGGACGCTCCAACAGTGGTGAAGAAGCCAGAATTACAGGGGAGTTAATG
GTACAGAGCCAGCTGTTCATGAAGGAGAGTGACCTCCTAGCTTCACTAGGACTAAGCTTTCTCCTTGGTCTGTTTACGCTAGGGAAAAGAGAGGAACAAGGAGCGATCAGAACCGA
CTGAAACAGGAAACAAGGAGAGTGACCTCCTAGCTTCACTAGGACTAAGCTTTCTCCTTGGTCTGTTTACGCTAGGGAAAAGAGAGAACAAGGAGCGATCAGAACCGA
CCGGTGGCCATCACCATCACCATCACCATCATTAATTAAGTCTAGAGATCC

SEQ ID NO: 4 (NanA coding sequence)

MKKIWLALAG LVLAFSASAA QGDQNATGG EQPLANETQL SGESSTLIDT EKSQPSSETE LSGNKQEQER KDKQEEKIPR DYYARDLENV ETVIEKEDVE
TNASNGQRVD LSSELDKLKK LENATVHMEF KPDAKAPAFY NLFSVSSATK KDEYFTMAVY NNTATLEGRG SDGKQFYNNY NDAPLKVKPG QWNSVTFTVE
KPTAELPKGR VRLYVNGVLS RTSLRSGNFI KDMPDVTHVQ IGATKRANNT VWGSNLQIRN LTVVNRALTP EEVQKRSQLF KRSDLEKKLP EGAALTEKTD
IFESGRNGKP NKDGIKSYRI PALLKTDKGT LIAGADERRL HSSDWDGIGM VIRRSEDNGK TWGDRVTITN LRDNPKASDP SIGSPVNIDM VLVQDPETKR
IFSIYDMFPE GKGIFGMSSQ KEEAYKKIDG KTYQILYREG EKGAYTIREN GTVYTPDGKA TDYRVVVDPV KPAYSDKGDL YKGNQLLGNI YFTTNKTSPF
RIAKDSYLWM SYSDDDGKTW SAPQDITPMV KADWMKFLGV GPGTGIVLRN GPHKGRILIP VYTTNNVSHL NGSQSSRIIY SDDHGKTWHA GEAVNDNRQV
DGQKIHSSTM NNRRAQNTES TVVQLNNGDV KLFMRGLTGD LQVATSKDGG VTWEKDIKRY PQVKDVYVQM SAIHTMHEGK EYIILSNAGG PKRENGMVHL
ARVEENGELT WLKHNPIQKG EFAYNSLQEL GNGEYGILYE HTEKGQNAYT LSFRKFNWDF LSKDLISPTE AKVKRTREMG KGVIGLEFDS EVLVNKAPTL
QLANGKTARF MTQYDTKTLL FTVDSEDMGQ KVTGLAEGAI ESMHNLPVSV AGTKLSNGMN GSEAAVHEVP EYTGPLGTSG EEPAPTVEKP EYTGPLGTSG
EEPAPTVEKP EFTGGVNGTE PAVHEIAEYK GSDSLVTLTT KEDYTYKAPL AQQALPETGN KESDLLASLG LTAFFLGLFT
LGKKREQGGD QNATGGHHHH HHHHHH

SEQ ID NO: 5 NanA amino acid sequence with sequons (solid underline), His tag (italics) and leader peptide
(dotted underline).

EQPLANETQL SGESSTLIDT EKSQPSSETE LSGNKQEQER KDKQEEKIPR DYYARDLENV ETVIEKEDVE TNASNGQRVD LSSELDKLKK LENATVHMEF
KPDAKAPAFY NLFSVSSATK KDEYFTMAVY NNTATLEGRG SDGKQFYNNY NDAPLKVKPG QWNSVTFTVE KPTAELPKGR VRLYVNGVLS RTSLRSGNFI
KDMPDVTHVQ IGATKRANNT VWGSNLQIRN LTVVNRALTP EEVQKRSQLF KRSDLEKKLP EGAALTEKTD IFESGRNGKP NKDGIKSYRI PALLKTDKGT
LIAGADERRL HSSDWDGIGM VIRRSEDNGK TWGDRVTITN LRDNPKASDP SIGSPVNIDM VLVQDPETKR IFSIYDMFPE GKGIFGMSSQ KEEAYKKIDG
KTYQILYREG EKGAYTIREN GTVYTPDGKA TDYRVVVDPV KPAYSDKGDL YKGNQLLGNI YFTTNKTSPF RIAKDSYLWM SYSDDDGKTW SAPQDITPMV
KADWMKFLGV GPGTGIVLRN GPHKGRILIP VYTTNNVSHL NGSQSSRIIY SDDHGKTWHA GEAVNDNRQV DGQKIHSSTM NNRRAQNTES TVVQLNNGDV
KLFMRGLTGD LQVATSKDGG VTWEKDIKRY PQVKDVYVQM SAIHTMHEGK EYIILSNAGG PKRENGMVHL ARVEENGELT WLKHNPIQKG EFAYNSLQEL
GNGEYGILYE HTEKGQNAYT LSFRKFNWDF LSKDLISPTE AKVKRTREMG KGVIGLEFDS EVLVNKAPTL QLANGKTARF MTQYDTKTLL FTVDSEDMGQ
KVTGLAEGAI ESMHNLPVSV AGTKLSNGMN GSEAAVHEVP EYTGPLGTSG EEPAPTVEKP EYTGPLGTSG EEAAPTVEKP EFTGGVNGTE PAVHEIAEYK
GSDSLVTLTT KEDYTYKAPL AQQALPETGN KESDLLASLG LTAFFLGLFT LGKKREQ

SEQ ID NO: 6 (NanA amino acid sequence)

GGATCCGAATTCCATTTTAAATAAGGAGAATAACATAATGAAAAAGATTTGGCTGGCGCTGGCTGGTTGCTCAGGGGTGCTAAGAAGAAGCAGCTAGCAAGAAGAAGAAATCATCGTTGCAA
ACGCGACCGGTGGCCATCACCATCACCATCACCATCATTAATTAAGTCTAGAGATCCCAATGGATCCGTCCAAAGCACCATTATCTATGCATGAAGAGAAATGACGAATTGACTGGTTACGACCGTCGGTGGTTGAGTCGTTCGCCTATCTTAAAGATTCTGACAAATATGATGTCAAGTTG
AAAAGACAGAATGTCAGGTGTCTTTGCTGTCATGCTGTTACACTGGCTCTGACATGGCTCACAATCTAGCTACACTAAAGAACGTGCGGAGAAATACCTCTATGCCGCAC
CAATTGCCCAAAATCCTAATGTCCTTGCTGAACACGACAACTGAACAACAGACAGCACCTCGATGAAATCGACGAAGTCGTTCAAGCGAAGTCGTTCAAGCGATGGAACAATTTGACTATA
AGAAGTTTGATAAGCACATACAAATGCGGTTGTGAACAGACCATTGCTAAGGCAGATTGCAACCTTGACAGACAGCCTCCAAGCGACCAAAGCCTCGTTTTACCCACTTCTTGCTC
AGGGTCAAGATGAGTTGAAATCGTTTGTGACAAATCGCATCAAGACAACTTTATAAGATGAAGAACTGTCTAAACAATGGAAGACAATGCTAAACAATTGTCTAAACAATTCTTCGGAGAACACTTATCTACCGGCAG
AAGCTCTGATATTTAAAGGAGGGCGATCAAGATCTAGAGAGAATGTT

-continued

Sequences

SEQ ID NO: 7 Sp0148 coding sequence

<u>MKKIWLALAG LVILAFSASAA QGGDQNATGG AALALVAAGV LAACSGGAKK EGEAASKKEI IVATNGSPKP FIYEENGELT</u>
FEKTEWSGVF AGLDADRYNM AVNNLSYTKE RAEKYLYAAP IAQNPNVLVV KKDDSSIKSL DDIGGKSTEV VQATTSAKQL EAYNAEHTDN PTILNYTKAD
LQQIMVRLSD GQFDYKIFDK IGVETVIKNQ GLDNLKVIEL PSDQQPYVYP LLAQGQDELK SFVDKRIKEL YKDGTLEKLS KQFFGDTYLP AEADIKGGDQ
NATG*HHHHH HHHHH*
SEQ ID NO: 8 Sp0148 amino acid sequence with sequons (solid underline), His tag (italics) and leader peptide (dotted underline).

AALALVAAGV LAACSGGAKK EGEAASKKEI IVATNGSPKP FIYEENGELT GYEIEVVRAI FKDSDKYDVK FEKTEWSGVF AGLDADRYNM AVNNLSYTKE
RAEKYLYAAP IAQNPNVLVV KKDDSSIKSL DDIGGKSTEV VQATTSAKQL EAYNAEHTDN PTILNYTKAD LQQIMVRLSD GQFDYKIFDK IGVETVIKNQ
GLDNLKVIEL PSDQQPYVYP LLAQGQDELK SFVDKRIKEL YKDGTLEKLS KQFFGDTYLP AEADIK
SEQ ID NO: 9 (Sp0148 amino acid sequence)

1 mlkkeylknp ylvlfamiil ayvfsvfcrf ywvwasefn eyffnnqlmi isndgyafae
 61 gardmiagfh qppdlsyygs slstltywly kitpfsfesi vlymstflss lvvipiilla
121 neykrplmgf vaallasian syynrtmsgy ydtdmlvivl pmfilffmvr milkkdffsl
181 ialplfigiy lwwypssytl nvaliglfli ytlifhrkek ifyiavisss ltlsniawfy
241 qsaiivilfa ifaleqkrln fmiigilgsv gseivflfsl fgfawlirkh ksmimalpil
301 ltgfmyfnv ngtiqevenv dlsefmrris malgfgflls efkailvkky sqltsnvciv fatiltlapv
361 vlgflalkgg lrftiysvpv lnqlknianr edyvvtwwdy gypvryysdv ktlvdggkhl
421 fihiynykap tvfsqneasl lskdeqaaan marlsveyte ksfyalqndi lktdilqamm kdynqsnvdl
481 gkdniffpsfa kidtpktrdi ylymparmsl ifstvasfaf inldtgvldk pftfstaypl
541 flaslskpdf dvkingeiyls ngvvlsddfir sfkigdnvvs vnsiveinsi kqgeykitpi ddkaqfyify
601 lkdsaipyaq filmdktmfn sayvqmfflg nydknlfdsv insrdakvfk lki
SEQ ID NO: 10 (Campylobacter jejuni PglB amino acid sequence)

The invention claimed is:

1. A glycoconjugate comprising an isolated *S. pneumoniae* protein antigen glycosylated with an isolated *S. pneumoniae* capsular polysaccharide, wherein the isolated protein antigen is *S. pneumoniae* PiuA protein antigen comprising an amino acid sequence having at least 80% sequence identity to SEQ ID NO: 3, protein antigen comprises a heterologous glycosylation sequon, wherein the heterologous glycosylation sequon comprises the sequence D/E-Y-N-X-S/T, wherein Y and X are any amino acid except P (SEQ ID NO: 11).

2. The glycoconjugate according to claim 1, wherein the protein antigen comprises a heterologous glycosylation sequon, wherein the heterologous glycosylation sequon comprises the sequence D/E-Y-N-X-S/T, wherein Y and X are any amino acid except P (SEQ ID NO: 11).

3. The glycoconjugate according to claim 2, wherein the protein antigen comprises two or more of the heterologous glycosylation sequons.

4. The glycoconjugate according to claim 2, wherein the PiuA protein antigen comprises an amino acid sequence having at least 80% sequence identity to SEQ ID NO: 2.

5. The glycoconjugate according to claim 1, wherein the capsular polysaccharide is *S. pneumoniae* serotype 4 capsular polysaccharide.

6. A vaccine composition comprising the glycoconjugate according to claim 1 and a pharmaceutically acceptable excipient.

7. The vaccine composition according to claim 6 further comprising an adjuvant.

8. The glycoconjugate of claim 1, wherein the glycoconjugate is a recombinant glycoconjugate and wherein the isolated *S. pneumoniae* PiuA protein antigen comprises the amino acid sequence of SEQ ID NO: 3 and the isolated capsular polysaccharide is serotype 4 *S. pneumoniae* capsular polysaccharide.

9. A vaccine composition comprising the glycoconjugate according to claim 8 and a pharmaceutically acceptable excipient.

10. The vaccine composition according to claim 9 further comprising an adjuvant.

11. A method of generating an immune response against *S. pneumoniae* in a mammalian subject comprising administering to the mammalian subject an effective amount of the composition of claim 6.

12. A method of protecting a mammalian subject against *S. pneumoniae* infection comprising administering to the mammalian subject an effective amount of the composition of claim 9, wherein the mammalian subject is susceptible to or is at risk of *S. pneumoniae* infection.

* * * * *

UNITED STATES PATENT AND TRADEMARK OFFICE
CERTIFICATE OF CORRECTION

PATENT NO. : 12,048,743 B2
APPLICATION NO. : 17/052485
DATED : July 30, 2024
INVENTOR(S) : Brendan Wren, Jeremy Brown and Jon Cuccui It is certified that error appears in the above-identified patent and that said Letters Patent is hereby corrected as shown below:

In the Claims

In Claim 1:
"1. A glycoconjugate comprising an isolated S. pneumoniae protein antigen glycosylated with an isolated S. pneumoniae capsular polysaccharide, wherein the isolated protein antigenis S. pneumoniae PiuA protein antigen comprising an amino acid sequence having at least 80% sequence identity to SEQ ID NO: 3,
protein antigen comprises a heterologous glycosylation sequon, wherein the heterologous glycosylation sequon comprises the sequence D/E-Y-N-X-S/T, wherein Y and X are any amino acid except P (SEQIDNO:11)."

Should be changed to:
--1. A glycoconjugate comprising an isolated S. pneumoniae protein antigen glycosylated with an isolated S. pneumoniae capsular polysaccharide, wherein the isolated protein antigenis S. pneumoniae PiuA protein antigen comprising an amino acid sequence having at least 80% sequence identity to SEQ ID NO: 3.--

Signed and Sealed this
Seventeenth Day of September, 2024

Katherine Kelly Vidal
*Director of the United States Patent and Trademark Office*

SEQUENCE LISTING

<160> NUMBER OF SEQ ID NOS: 41

<210> SEQ ID NO 1
<211> LENGTH: 1138
<212> TYPE: DNA
<213> ORGANISM: Artificial Sequence
<220> FEATURE:
<223> OTHER INFORMATION: (PiuA coding sequence) with sequons

<400> SEQUENCE: 1

| | | | | | |
|---|---|---|---|---|---|
| ggatccgaat | tccattttaa | ataaggagga | ataacataat | gaaaaagatt | tggctggcgc | 60 |
| tggctggttt | agtttagcg | tttagcgcat | cggcggcgca | gggaggcgat | cagaacgcga | 120 |
| ccggtggcgc | cctagtggcc | agcttcttgc | tcctacttgg | tgcatgtagt | acaaactcaa | 180 |
| gcactagtca | gacagagacc | agtagctctg | ctccaacaga | ggtaaccatt | aaaagttcac | 240 |
| tggacgaggt | caaactttcc | aaagttcctg | aaaagattgt | gacctttgac | ctcggcgctg | 300 |
| cggatactat | tcgcgcttta | ggatttgaaa | aaatatcgt | cggaatgcct | acaaaaactg | 360 |
| ttccgactta | tctaaaagac | ctagtgggaa | ctgtcaaaaa | tgttggttct | atgaaagaac | 420 |
| ctgatttaga | agctatcgcc | gcccttgagc | ctgatttgat | tatcgcttcg | ccacgtacac | 480 |
| aaaaattcgt | agacaaattc | aaagaaatcg | ccccaaccgt | tctcttccaa | gcaagcaagg | 540 |
| acgactactg | gacttctacc | aaggctaata | tcgaatcctt | agcaagtgcc | ttcggcgaaa | 600 |
| ctggtacaca | gaaagccaag | gaagaattga | ccaagctaga | caagagcatc | caagaagtcg | 660 |
| ctactaaaaa | tgaaagctct | gacaaaaaag | cccttgcgat | cctccttaat | gaaggaaaaa | 720 |
| tggcagcctt | tggtgccaaa | tctcgtttct | cttttcttgta | ccaaaccttg | aaattcaaac | 780 |
| caactgatac | aaaatttgaa | gactcacgcc | acggacaaga | agtcagcttt | gaaagtgtca | 840 |
| aagaaatcaa | ccctgacatc | ctctttgtca | tcaaccgtac | ccttgccatc | ggtggggaca | 900 |
| actctagcaa | cgacggtgtc | ctagaaaatg | cccttatcgc | tgaaacacct | gctgctaaaa | 960 |
| atggtaagat | tatccaacta | acaccagacc | tctggtatct | aagcggaggc | ggacttgaat | 1020 |
| caacaaaact | catgattgaa | gacatacaaa | aagctttgaa | aggaggcgat | cagaacgcga | 1080 |
| ccggtggcca | tcaccatcat | caccatcatc | accatcatta | attaagtcta | gaggatcc | 1138 |

<210> SEQ ID NO 2
<211> LENGTH: 360
<212> TYPE: PRT
<213> ORGANISM: Artificial Sequence
<220> FEATURE:
<223> OTHER INFORMATION: 2 PiuA amino acid sequence with sequons,His tag
      and leader peptide

<400> SEQUENCE: 2

Met Lys Lys Ile Trp Leu Ala Leu Ala Gly Leu Val Leu Ala Phe Ser
1               5                   10                  15

Ala Ser Ala Ala Gln Gly Gly Asp Gln Asn Ala Thr Gly Gly Ala Leu
            20                  25                  30

Val Ala Ser Phe Leu Leu Leu Gly Ala Cys Ser Thr Asn Ser Ser
        35                  40                  45

Thr Ser Gln Thr Glu Thr Ser Ser Ala Pro Thr Glu Val Thr Ile
    50                  55                  60

Lys Ser Ser Leu Asp Glu Val Lys Leu Ser Lys Val Pro Glu Lys Ile
65                  70                  75                  80

Val Thr Phe Asp Leu Gly Ala Ala Asp Thr Ile Arg Ala Leu Gly Phe
                85                  90                  95

```
Glu Lys Asn Ile Val Gly Met Pro Thr Lys Thr Val Pro Thr Tyr Leu
                100                 105                 110

Lys Asp Leu Val Gly Thr Val Lys Asn Val Gly Ser Met Lys Glu Pro
            115                 120                 125

Asp Leu Glu Ala Ile Ala Ala Leu Glu Pro Asp Leu Ile Ile Ala Ser
        130                 135                 140

Pro Arg Thr Gln Lys Phe Val Asp Lys Phe Lys Glu Ile Ala Pro Thr
145                 150                 155                 160

Val Leu Phe Gln Ala Ser Lys Asp Tyr Trp Thr Ser Thr Lys Ala
                165                 170                 175

Asn Ile Glu Ser Leu Ala Ser Ala Phe Gly Glu Thr Gly Thr Gln Lys
                180                 185                 190

Ala Lys Glu Glu Leu Thr Lys Leu Asp Lys Ser Ile Gln Glu Val Ala
            195                 200                 205

Thr Lys Asn Glu Ser Ser Asp Lys Lys Ala Leu Ala Ile Leu Leu Asn
        210                 215                 220

Glu Gly Lys Met Ala Ala Phe Gly Ala Lys Ser Arg Phe Ser Phe Leu
225                 230                 235                 240

Tyr Gln Thr Leu Lys Phe Lys Pro Thr Asp Thr Lys Phe Glu Asp Ser
                245                 250                 255

Arg His Gly Gln Glu Val Ser Phe Glu Ser Val Lys Glu Ile Asn Pro
                260                 265                 270

Asp Ile Leu Phe Val Ile Asn Arg Thr Leu Ala Ile Gly Gly Asp Asn
                275                 280                 285

Ser Ser Asn Asp Gly Val Leu Glu Asn Ala Leu Ile Ala Glu Thr Pro
            290                 295                 300

Ala Ala Lys Asn Gly Lys Ile Ile Gln Leu Thr Pro Asp Leu Trp Tyr
305                 310                 315                 320

Leu Ser Gly Gly Gly Leu Glu Ser Thr Lys Leu Met Ile Glu Asp Ile
                325                 330                 335

Gln Lys Ala Leu Lys Gly Gly Asp Gln Asn Ala Thr Gly Gly His His
            340                 345                 350

His His His His His His
        355                 360

<210> SEQ ID NO 3
<211> LENGTH: 311
<212> TYPE: PRT
<213> ORGANISM: Artificial Sequence
<220> FEATURE:
<223> OTHER INFORMATION: (PiuA amino acid sequence)

<400> SEQUENCE: 3

Ala Leu Val Ala Ser Phe Leu Leu Leu Gly Ala Cys Ser Thr Asn
1               5                   10                  15

Ser Ser Thr Ser Gln Thr Glu Thr Ser Ser Ser Ala Pro Thr Glu Val
            20                  25                  30

Thr Ile Lys Ser Ser Leu Asp Glu Val Lys Leu Ser Lys Val Pro Glu
        35                  40                  45

Lys Ile Val Thr Phe Asp Leu Gly Ala Ala Asp Thr Ile Arg Ala Leu
    50                  55                  60

Gly Phe Glu Lys Asn Ile Val Gly Met Pro Thr Lys Thr Val Pro Thr
65                  70                  75                  80

Tyr Leu Lys Asp Leu Val Gly Thr Val Lys Asn Val Gly Ser Met Lys
                85                  90                  95
```

```
Glu Pro Asp Leu Glu Ala Ile Ala Ala Leu Glu Pro Asp Leu Ile Ile
            100                 105                 110

Ala Ser Pro Arg Thr Gln Lys Phe Val Asp Lys Phe Lys Glu Ile Ala
        115                 120                 125

Pro Thr Val Leu Phe Gln Ala Ser Lys Asp Asp Tyr Trp Thr Ser Thr
    130                 135                 140

Lys Ala Asn Ile Glu Ser Leu Ala Ser Ala Phe Gly Glu Thr Gly Thr
145                 150                 155                 160

Gln Lys Ala Lys Glu Leu Thr Lys Leu Asp Lys Ser Ile Gln Glu
                165                 170                 175

Val Ala Thr Lys Asn Glu Ser Ser Asp Lys Lys Ala Leu Ala Ile Leu
            180                 185                 190

Leu Asn Glu Gly Lys Met Ala Ala Phe Gly Ala Lys Ser Arg Phe Ser
        195                 200                 205

Phe Leu Tyr Gln Thr Leu Lys Phe Lys Pro Thr Asp Thr Lys Phe Glu
    210                 215                 220

Asp Ser Arg His Gly Gln Glu Val Ser Phe Glu Ser Val Lys Glu Ile
225                 230                 235                 240

Asn Pro Asp Ile Leu Phe Val Ile Asn Arg Thr Leu Ala Ile Gly Gly
                245                 250                 255

Asp Asn Ser Ser Asn Asp Gly Val Leu Glu Asn Ala Leu Ile Ala Glu
            260                 265                 270

Thr Pro Ala Ala Lys Asn Gly Lys Ile Ile Gln Leu Thr Pro Asp Leu
        275                 280                 285

Trp Tyr Leu Ser Gly Gly Leu Glu Ser Thr Lys Leu Met Ile Glu
    290                 295                 300

Asp Ile Gln Lys Ala Leu Lys
305                 310

<210> SEQ ID NO 4
<211> LENGTH: 3136
<212> TYPE: DNA
<213> ORGANISM: Artificial Sequence
<220> FEATURE:
<223> OTHER INFORMATION: NanA coding sequence

<400> SEQUENCE: 4
ggatccgaat tccattttaa ataaggagga ataacataat gaaaaagatt tggctggcgc      60
tggctggttt agtttttagcg tttagcgcat cggcggcgca gggaggcgat cagaacgcga     120
ccggtggcga gcaacctctg gcaaatgaaa ctcaactttc gggggagagc tcaaccctaa     180
ctgatacaga aaagagccag ccttcttcag agactgaact ttctggcaat aagcaagaac     240
aagaaaggaa agataagcaa gaagaaaaaa ttccaagaga ttactatgca cgagatttgg     300
aaaatgtcga acagtgata gaaaagaag atgttgaaac caatgcttca aatggtcaga     360
gagttgattt atcaagtgaa ctagataaac taaagaaact tgaaaacgca acagttcaca     420
tggagtttaa gccagatgcc aaggcccag cattctataa tctctttct gtgtcaagtg      480 ctactaaaaa agatgagtac ttcactatgg cagtttacaa taatactgct accctagagg     540
ggcgtggttc ggatgggaaa cagttttaca ataattacaa cgatgcaccc ttaaaagtta     600
aaccaggtca gtggaactct gtgactttca cagttgaaaa accgacagca gaactaccta     660
aaggccgagt cgcctctac gtaaacgggg tattatctcg aacaagtctg agatctggca     720
atttcattaa agatatgcca gatgtaacgc atgtgcaaat cggagcaacc aagcgtgcca     780
acaatacggt ttgggggtca atctacagat tcggaatct cactgtgtat aatcgtgctt     840
```

```
taacaccaga agaggtacaa aaacgtagtc aacttttaa acgctcagat ttagaaaaaa      900
aactacctga aggagcggct ttaacagaga aaacggacat attcgaaagc gggcgtaacg      960
gtaaaccaaa taagatgga atcaagagtt atcgtattcc agcacttctc aagacagata     1020
aaggaacttt gatcgcaggt gcagatgaac gccgtctcca ttcgagtgac tggggtgata     1080
tcggtatggt catcagacgt agtgaagata atggtaaaac ttggggtgac cgagtaacca     1140
ttaccaactt acgtgacaat ccaaaagctt ctgacccatc gatcggttca ccagtgaata     1200
tcgatatggt gttggttcaa gatcctgaaa ccaaacgaat ctttctatc tatgacatgt      1260
tcccagaagg gaagggaatc tttgaatgt cttcacaaaa agaagaagcc tacaaaaaaa      1320
tcgatggaaa aacctatcaa atcctctatc gtgaaggaga aaagggagct tataccattc     1380
gagaaaatgg tactgtctat acaccagatg gtaaggcgac agactatcgc gttgttgtag     1440
atcctgttaa accagcctat agcgacaagg gggatctata caagggtaac caattactag     1500
gcaatatcta cttcacaaca aacaaaactt ctccatttag aattgccaag gatagctatc     1560
tatggatgtc ctacagtgat gacgacggga agacatggtc agcgcctcaa gatattactc     1620
cgatggtcaa agccgattgg atgaaattct tgggtgtagg tcctggaaca ggaattgtac     1680
ttcggaatgg gcctcacaag ggacggattt tgataccggt ttatacgact aataatgtat     1740
ctcacttaaa tggctcgcaa tcttctcgta tcatctattc agatgatcat ggaaaaactt     1800
ggcatgctgg agaagcggtc aacgataacc gtcaggtaga cggtcaaaag atccactctt     1860
ctacgatgaa caatagacgt gcgcaaaata cagaatcaac ggtggtacaa ctaaacaatg     1920
gagatgttaa actctttatg cgtggtttga ctggagatct tcaggttgct acaagtaaag     1980
acggaggagt gacttgggag aaggatatca aacgttatcc acaggttaaa gatgtctatg     2040
ttcaaatgtc tgctatccat acgatgcacg aaggaaaaga atacatcatc ctcagtaatg     2100
caggtggacc gaaacgtgaa aatgggatgg tccacttggc acgtgtcgaa gaaaatggtg     2160
agttgacttg gctcaaacac aatccaattc aaaaaggaga gtttgcctat aattcgctcc     2220
aagaattagg aaatgggag tatggcatct tgtatgaaca tactgaaaaa ggacaaaatg      2280
cctataccct atcatttaga aaatttaatt gggactttt gagcaaagat ctgatttctc      2340
ctaccgaagc gaaagtgaag cgaactagag agatgggcaa aggagttatt ggcttggagt     2400
tcgactcaga agtattggtc aacaaggctc caacccttca attggcaaat ggtaaaacag     2460
cacgcttcat gacccagtat gatacaaaaa ccctcctatt tacagtggat tcagaggata     2520
tgggtcaaaa agttacaggt ttggcagaag gtgcaattga agtatgcat aatttaccag      2580
tctctgtggc gggcactaag ctttcgaatg gaatgaacgg aagtgaagct gctgttcatg     2640
aagtgccaga atacacaggc ccattaggga catccggcga agagccagct ccaacagtcg     2700
agaagccaga atacacaggc ccactaggga catccggcga agagccagcc cgacagtcg      2760
agaagccaga atacacaggc ccactaggga cagctggtga agaagcagct ccaacagtcg     2820
agaagccaga atttacaggg ggagttaatg gtacagagcc agctgttcat gaaatcgcag     2880
agtataaggg atctgattcg cttgtaactc ttactacaaa agaagattat acttacaaag     2940
ctcctcttgc tcagcaggca cttcctgaaa caggaaacaa ggagagtgac ctcctagctt     3000
cactaggact aacagctttc ttccttggtc tgtttacgct agggaaaaag agagaacaag     3060
gaggcgatca gaacgcgacc ggtggccatc accatcatca ccatcatcac catcattaat     3120
taagtctaga ggatcc                                                    3136
```

<210> SEQ ID NO 5
<211> LENGTH: 1026
<212> TYPE: PRT
<213> ORGANISM: Artificial Sequence
<220> FEATURE:
<223> OTHER INFORMATION: NanA amino acid sequence with sequons, His tag
      and leader peptide

<400> SEQUENCE: 5

```
Met Lys Lys Ile Trp Leu Ala Leu Ala Gly Leu Val Leu Ala Phe Ser
1               5                   10                  15

Ala Ser Ala Ala Gln Gly Gly Asp Gln Asn Ala Thr Gly Gly Glu Gln
            20                  25                  30

Pro Leu Ala Asn Glu Thr Gln Leu Ser Gly Glu Ser Ser Thr Leu Thr
        35                  40                  45

Asp Thr Glu Lys Ser Gln Pro Ser Ser Glu Thr Glu Leu Ser Gly Asn
50                  55                  60

Lys Gln Glu Gln Glu Arg Lys Asp Lys Gln Glu Lys Ile Pro Arg
65                  70                  75                  80

Asp Tyr Tyr Ala Arg Asp Leu Glu Asn Val Glu Thr Val Ile Glu Lys
                85                  90                  95

Glu Asp Val Glu Thr Asn Ala Ser Asn Gly Gln Arg Val Asp Leu Ser
            100                 105                 110

Ser Glu Leu Asp Lys Leu Lys Lys Leu Glu Asn Ala Thr Val His Met
        115                 120                 125

Glu Phe Lys Pro Asp Ala Lys Ala Pro Ala Phe Tyr Asn Leu Phe Ser
130                 135                 140

Val Ser Ser Ala Thr Lys Lys Asp Glu Tyr Phe Thr Met Ala Val Tyr
145                 150                 155                 160

Asn Asn Thr Ala Thr Leu Glu Gly Arg Gly Ser Asp Gly Lys Gln Phe
                165                 170                 175

Tyr Asn Asn Tyr Asn Asp Ala Pro Leu Lys Val Lys Pro Gly Gln Trp
            180                 185                 190

Asn Ser Val Thr Phe Thr Val Glu Lys Pro Thr Ala Glu Leu Pro Lys
        195                 200                 205

Gly Arg Val Arg Leu Tyr Val Asn Gly Val Leu Ser Arg Thr Ser Leu
210                 215                 220

Arg Ser Gly Asn Phe Ile Lys Asp Met Pro Asp Val Thr His Val Gln
225                 230                 235                 240

Ile Gly Ala Thr Lys Arg Ala Asn Asn Thr Val Trp Gly Ser Asn Leu
                245                 250                 255

Gln Ile Arg Asn Leu Thr Val Tyr Asn Arg Ala Leu Thr Pro Glu Glu
            260                 265                 270

Val Gln Lys Arg Ser Gln Leu Phe Lys Arg Ser Asp Leu Glu Lys Lys
        275                 280                 285

Leu Pro Glu Gly Ala Ala Leu Thr Glu Lys Thr Asp Ile Phe Glu Ser
290                 295                 300

Gly Arg Asn Gly Lys Pro Asn Lys Asp Gly Ile Lys Ser Tyr Arg Ile
305                 310                 315                 320

Pro Ala Leu Leu Lys Thr Asp Lys Gly Thr Leu Ile Ala Gly Ala Asp
                325                 330                 335

Glu Arg Arg Leu His Ser Ser Asp Trp Gly Asp Ile Gly Met Val Ile
            340                 345                 350

Arg Arg Ser Glu Asp Asn Gly Lys Thr Trp Gly Asp Arg Val Thr Ile
        355                 360                 365
```

```
Thr Asn Leu Arg Asp Asn Pro Lys Ala Ser Asp Pro Ser Ile Gly Ser
    370                 375                 380

Pro Val Asn Ile Asp Met Val Leu Val Gln Asp Pro Glu Thr Lys Arg
385                 390                 395                 400

Ile Phe Ser Ile Tyr Asp Met Phe Pro Glu Gly Lys Gly Ile Phe Gly
                405                 410                 415

Met Ser Ser Gln Lys Glu Glu Ala Tyr Lys Lys Ile Asp Gly Lys Thr
                420                 425                 430

Tyr Gln Ile Leu Tyr Arg Glu Gly Lys Gly Ala Tyr Thr Ile Arg
            435                 440                 445

Glu Asn Gly Thr Val Tyr Thr Pro Asp Gly Lys Ala Thr Asp Tyr Arg
    450                 455                 460

Val Val Val Asp Pro Val Lys Pro Ala Tyr Ser Asp Lys Gly Asp Leu
465                 470                 475                 480

Tyr Lys Gly Asn Gln Leu Leu Gly Asn Ile Tyr Phe Thr Thr Asn Lys
                485                 490                 495

Thr Ser Pro Phe Arg Ile Ala Lys Asp Ser Tyr Leu Trp Met Ser Tyr
                500                 505                 510

Ser Asp Asp Gly Lys Thr Trp Ser Ala Pro Gln Asp Ile Thr Pro
            515                 520                 525

Met Val Lys Ala Asp Trp Met Lys Phe Leu Gly Val Gly Pro Gly Thr
    530                 535                 540

Gly Ile Val Leu Arg Asn Gly Pro His Lys Gly Arg Ile Leu Ile Pro
545                 550                 555                 560

Val Tyr Thr Thr Asn Asn Val Ser His Leu Asn Gly Ser Gln Ser Ser
                565                 570                 575

Arg Ile Ile Tyr Ser Asp Asp His Gly Lys Thr Trp His Ala Gly Glu
            580                 585                 590

Ala Val Asn Asp Asn Arg Gln Val Asp Gly Gln Lys Ile His Ser Ser
    595                 600                 605

Thr Met Asn Asn Arg Arg Ala Gln Asn Thr Glu Ser Thr Val Val Gln
    610                 615                 620

Leu Asn Asn Gly Asp Val Lys Leu Phe Met Arg Gly Leu Thr Gly Asp
625                 630                 635                 640

Leu Gln Val Ala Thr Ser Lys Asp Gly Gly Val Thr Trp Glu Lys Asp
            645                 650                 655

Ile Lys Arg Tyr Pro Gln Val Lys Asp Val Tyr Val Gln Met Ser Ala
            660                 665                 670

Ile His Thr Met His Glu Gly Lys Glu Tyr Ile Ile Leu Ser Asn Ala
        675                 680                 685

Gly Gly Pro Lys Arg Glu Asn Gly Met Val His Leu Ala Arg Val Glu
    690                 695                 700

Glu Asn Gly Glu Leu Thr Trp Leu Lys His Asn Pro Ile Gln Lys Gly
705                 710                 715                 720

Glu Phe Ala Tyr Asn Ser Leu Gln Glu Leu Gly Asn Gly Glu Tyr Gly
                725                 730                 735

Ile Leu Tyr Glu His Thr Glu Lys Gly Gln Asn Ala Tyr Thr Leu Ser
                740                 745                 750

Phe Arg Lys Phe Asn Trp Asp Phe Leu Ser Lys Asp Leu Ile Ser Pro
    755                 760                 765

Thr Glu Ala Lys Val Lys Arg Thr Arg Glu Met Gly Lys Gly Val Ile
    770                 775                 780
```

```
Gly Leu Glu Phe Asp Ser Glu Val Leu Val Asn Lys Ala Pro Thr Leu
785                 790                 795                 800

Gln Leu Ala Asn Gly Lys Thr Ala Arg Phe Met Thr Gln Tyr Asp Thr
            805                 810                 815

Lys Thr Leu Leu Phe Thr Val Asp Ser Glu Asp Met Gly Gln Lys Val
        820                 825                 830

Thr Gly Leu Ala Glu Gly Ala Ile Glu Ser Met His Asn Leu Pro Val
    835                 840                 845

Ser Val Ala Gly Thr Lys Leu Ser Asn Gly Met Asn Gly Ser Glu Ala
850                 855                 860

Ala Val His Glu Val Pro Glu Tyr Thr Gly Pro Leu Gly Thr Ser Gly
865                 870                 875                 880

Glu Glu Pro Ala Pro Thr Val Glu Lys Pro Glu Tyr Thr Gly Pro Leu
                885                 890                 895

Gly Thr Ser Gly Glu Glu Pro Ala Pro Thr Val Glu Lys Pro Glu Tyr
            900                 905                 910

Thr Gly Pro Leu Gly Thr Ala Gly Glu Glu Ala Ala Pro Thr Val Glu
        915                 920                 925

Lys Pro Glu Phe Thr Gly Gly Val Asn Gly Thr Glu Pro Ala Val His
    930                 935                 940

Glu Ile Ala Glu Tyr Lys Gly Ser Asp Ser Leu Val Thr Leu Thr Thr
945                 950                 955                 960

Lys Glu Asp Tyr Thr Tyr Lys Ala Pro Leu Ala Gln Ala Leu Pro
                965                 970                 975

Glu Thr Gly Asn Lys Glu Ser Asp Leu Leu Ala Ser Leu Gly Leu Thr
            980                 985                 990

Ala Phe Phe Leu Gly Leu Phe Thr  Leu Gly Lys Lys Arg  Glu Gln Gly
        995                 1000                1005

Gly Asp  Gln Asn Ala Thr Gly  Gly His His His  His His His
    1010             1015                 1020

His His  His
    1025

<210> SEQ ID NO 6
<211> LENGTH: 977
<212> TYPE: PRT
<213> ORGANISM: Artificial Sequence
<220> FEATURE:
<223> OTHER INFORMATION: NanA amino acid sequence

<400> SEQUENCE: 6

Glu Gln Pro Leu Ala Asn Glu Thr Gln Leu Ser Gly Glu Ser Ser Thr
1               5                   10                  15

Leu Thr Asp Thr Glu Lys Ser Gln Pro Ser Ser Glu Thr Glu Leu Ser
            20                  25                  30

Gly Asn Lys Gln Glu Gln Glu Arg Lys Asp Lys Gln Glu Glu Lys Ile
        35                  40                  45

Pro Arg Asp Tyr Tyr Ala Arg Asp Leu Glu Asn Val Glu Thr Val Ile
    50                  55                  60

Glu Lys Glu Asp Val Glu Thr Asn Ala Ser Asn Gly Gln Arg Val Asp
65                  70                  75                  80

Leu Ser Ser Glu Leu Asp Lys Leu Lys Leu Glu Asn Ala Thr Val
            85                  90                  95

His Met Glu Phe Lys Pro Asp Ala Lys Ala Pro Ala Tyr Asn Leu
        100                 105                 110
```

-continued

Phe Ser Val Ser Ser Ala Thr Lys Lys Asp Glu Tyr Phe Thr Met Ala
            115                 120                 125
Val Tyr Asn Asn Thr Ala Thr Leu Glu Gly Arg Gly Ser Asp Gly Lys
    130                 135                 140
Gln Phe Tyr Asn Tyr Asn Asp Ala Pro Leu Lys Val Lys Pro Gly
145                 150                 155                 160
Gln Trp Asn Ser Val Thr Phe Thr Val Glu Lys Pro Thr Ala Glu Leu
                165                 170                 175
Pro Lys Gly Arg Val Arg Leu Tyr Val Asn Gly Val Leu Ser Arg Thr
            180                 185                 190
Ser Leu Arg Ser Gly Asn Phe Ile Lys Asp Met Pro Asp Val Thr His
            195                 200                 205
Val Gln Ile Gly Ala Thr Lys Arg Ala Asn Asn Thr Val Trp Gly Ser
    210                 215                 220
Asn Leu Gln Ile Arg Asn Leu Thr Val Tyr Asn Arg Ala Leu Thr Pro
225                 230                 235                 240
Glu Glu Val Gln Lys Arg Ser Gln Leu Phe Lys Arg Ser Asp Leu Glu
                245                 250                 255
Lys Lys Leu Pro Glu Gly Ala Ala Leu Thr Glu Lys Thr Asp Ile Phe
            260                 265                 270
Glu Ser Gly Arg Asn Gly Lys Pro Asn Lys Asp Gly Ile Lys Ser Tyr
        275                 280                 285
Arg Ile Pro Ala Leu Leu Lys Thr Asp Lys Gly Thr Leu Ile Ala Gly
    290                 295                 300
Ala Asp Glu Arg Arg Leu His Ser Ser Asp Trp Gly Asp Ile Gly Met
305                 310                 315                 320
Val Ile Arg Arg Ser Glu Asp Asn Gly Lys Thr Trp Gly Asp Arg Val
                325                 330                 335
Thr Ile Thr Asn Leu Arg Asp Asn Pro Lys Ala Ser Asp Pro Ser Ile
            340                 345                 350
Gly Ser Pro Val Asn Ile Asp Met Val Leu Val Gln Asp Pro Glu Thr
        355                 360                 365
Lys Arg Ile Phe Ser Ile Tyr Asp Met Phe Pro Glu Gly Lys Gly Ile
    370                 375                 380
Phe Gly Met Ser Ser Gln Lys Glu Glu Ala Tyr Lys Lys Ile Asp Gly
385                 390                 395                 400
Lys Thr Tyr Gln Ile Leu Tyr Arg Glu Gly Glu Lys Gly Ala Tyr Thr
                405                 410                 415
Ile Arg Glu Asn Gly Thr Val Tyr Thr Pro Asp Gly Lys Ala Thr Asp
            420                 425                 430
Tyr Arg Val Val Asp Pro Val Lys Pro Ala Tyr Ser Asp Lys Gly
        435                 440                 445
Asp Leu Tyr Lys Gly Asn Gln Leu Leu Gly Asn Ile Tyr Phe Thr Thr
    450                 455                 460
Asn Lys Thr Ser Pro Phe Arg Ile Ala Lys Asp Ser Tyr Leu Trp Met
465                 470                 475                 480
Ser Tyr Ser Asp Asp Asp Gly Lys Thr Trp Ser Ala Pro Gln Asp Ile
                485                 490                 495
Thr Pro Met Val Lys Ala Asp Trp Met Lys Phe Leu Gly Val Gly Pro
            500                 505                 510
Gly Thr Gly Ile Val Leu Arg Asn Gly Pro His Lys Gly Arg Ile Leu
        515                 520                 525
Ile Pro Val Tyr Thr Thr Asn Asn Val Ser His Leu Asn Gly Ser Gln

```
            530                 535                 540
Ser Ser Arg Ile Ile Tyr Ser Asp Asp His Gly Lys Thr Trp His Ala
545                 550                 555                 560

Gly Glu Ala Val Asn Asp Asn Arg Gln Val Asp Gly Gln Lys Ile His
                565                 570                 575

Ser Ser Thr Met Asn Asn Arg Arg Ala Gln Asn Thr Glu Ser Thr Val
                580                 585                 590

Val Gln Leu Asn Asn Gly Asp Val Lys Leu Phe Met Arg Gly Leu Thr
                595                 600                 605

Gly Asp Leu Gln Val Ala Thr Ser Lys Asp Gly Val Thr Trp Glu
                610                 615                 620

Lys Asp Ile Lys Arg Tyr Pro Gln Val Lys Asp Val Tyr Val Gln Met
625                 630                 635                 640

Ser Ala Ile His Thr Met His Glu Gly Lys Glu Tyr Ile Ile Leu Ser
                645                 650                 655

Asn Ala Gly Gly Pro Lys Arg Glu Asn Gly Met Val His Leu Ala Arg
                660                 665                 670

Val Glu Glu Asn Gly Glu Leu Thr Trp Leu Lys His Asn Pro Ile Gln
                675                 680                 685

Lys Gly Glu Phe Ala Tyr Asn Ser Leu Gln Glu Leu Gly Asn Gly Glu
690                 695                 700

Tyr Gly Ile Leu Tyr Glu His Thr Glu Lys Gly Gln Asn Ala Tyr Thr
705                 710                 715                 720

Leu Ser Phe Arg Lys Phe Asn Trp Asp Phe Leu Ser Lys Asp Leu Ile
                725                 730                 735

Ser Pro Thr Glu Ala Lys Val Lys Arg Thr Arg Glu Met Gly Lys Gly
                740                 745                 750

Val Ile Gly Leu Glu Phe Asp Ser Glu Val Leu Val Asn Lys Ala Pro
                755                 760                 765

Thr Leu Gln Leu Ala Asn Gly Lys Thr Ala Arg Phe Met Thr Gln Tyr
                770                 775                 780

Asp Thr Lys Thr Leu Leu Phe Thr Val Asp Ser Glu Asp Met Gly Gln
785                 790                 795                 800

Lys Val Thr Gly Leu Ala Glu Gly Ala Ile Glu Ser Met His Asn Leu
                805                 810                 815

Pro Val Ser Val Ala Gly Thr Lys Leu Ser Asn Gly Met Asn Gly Ser
                820                 825                 830

Glu Ala Ala Val His Glu Val Pro Glu Tyr Thr Gly Pro Leu Gly Thr
                835                 840                 845

Ser Gly Glu Glu Pro Ala Pro Thr Val Glu Lys Pro Glu Tyr Thr Gly
850                 855                 860

Pro Leu Gly Thr Ser Gly Glu Glu Pro Ala Pro Thr Val Glu Lys Pro
865                 870                 875                 880

Glu Tyr Thr Gly Pro Leu Gly Thr Ala Gly Glu Glu Ala Pro Thr
                885                 890                 895

Val Glu Lys Pro Glu Phe Thr Gly Gly Val Asn Gly Thr Glu Pro Ala
                900                 905                 910

Val His Glu Ile Ala Glu Tyr Lys Gly Ser Asp Ser Leu Val Thr Leu
                915                 920                 925

Thr Thr Lys Glu Asp Tyr Thr Tyr Lys Ala Pro Leu Ala Gln Gln Ala
                930                 935                 940

Leu Pro Glu Thr Gly Asn Lys Glu Ser Asp Leu Leu Ala Ser Leu Gly
945                 950                 955                 960
```

Leu Thr Ala Phe Phe Leu Gly Leu Phe Thr Leu Gly Lys Lys Arg Glu
           965                 970                 975

Gln

<210> SEQ ID NO 7
<211> LENGTH: 1003
<212> TYPE: DNA
<213> ORGANISM: Artificial Sequence
<220> FEATURE:
<223> OTHER INFORMATION: Sp0148 coding sequence

<400> SEQUENCE: 7

```
ggatccgaat tccatttta  ataaggagga ataacataat gaaaaagatt tggctggcgc      60
tggctggttt agttttagcg tttagcgcat cggcggcgca gggaggcgat cagaacgcga     120
ccggtggcgc agcccttgct cttgttgctg caggtgtgct tgcggcttgc tcaggggtg     180
ctaagaaaga aggagaagca gctagcaaga aagaaatcat cgttgcaacc aatggatcac     240
caaagccatt tatctatgaa gaaaatggcg aattgactgg ttacgagatt gaagtcgttc     300
gcgctatctt taaagattct gacaaatatg atgtcaagtt tgaaaagaca gaatggtcag     360
gtgtctttgc tggtcttgac gctgatcgtt acaatatggc tgtcaacaat cttagctaca     420
ctaaagaacg tgcggagaaa tacctctatg ccgcaccaat tgcccaaaat cctaatgtcc     480
ttgtcgtgaa gaaagatgac tctagtatca agtctctcga tgatatcggt ggaaaatcga     540
cggaagtcgt tcaagccact acatcagcta agcagttaga agcatacaat gctgaacaca     600
cggacaaccc aactatcctt aactatacta aggcagactt gcaacaaatc atggtacgtt     660
tgagcgatgg acaatttgac tataagattt ttgataaaat cggtgttgaa acagtgatca     720
agaaccaagg tttggacaac ttgaaagtta tcgaacttcc aagcgaccaa caaccgtacg     780
tttacccact tcttgctcag ggtcaagatg agttgaaatc gtttgtagac aaacgcatca     840
aagaacttta taaagatgga actcttgaaa aattgtctaa acaattcttc ggagacactt     900
atctaccggc agaagctgat attaaggag gcgatcagaa cgcgaccggt ggccatcacc     960
atcatcacca tcatcaccat cattaattaa gtctagagga tcc                     1003
```

<210> SEQ ID NO 8
<211> LENGTH: 315
<212> TYPE: PRT
<213> ORGANISM: Artificial Sequence
<220> FEATURE:
<223> OTHER INFORMATION: Sp0148 amino acid sequence with sequons,His tag
       and leader peptide

<400> SEQUENCE: 8

Met Lys Lys Ile Trp Leu Ala Leu Ala Gly Leu Val Leu Ala Phe Ser
1               5                  10                  15

Ala Ser Ala Ala Gln Gly Gly Asp Gln Asn Ala Thr Gly Gly Ala Ala
           20                  25                  30

Leu Ala Leu Val Ala Ala Gly Val Leu Ala Ala Cys Ser Gly Gly Ala
       35                  40                  45

Lys Lys Glu Gly Glu Ala Ala Ser Lys Lys Glu Ile Ile Val Ala Thr
   50                  55                  60

Asn Gly Ser Pro Lys Pro Phe Ile Tyr Glu Glu Asn Gly Glu Leu Thr
65                  70                  75                  80

Gly Tyr Glu Ile Glu Val Val Arg Ala Ile Phe Lys Asp Ser Asp Lys
               85                  90                  95

```
Tyr Asp Val Lys Phe Glu Lys Thr Glu Trp Ser Gly Val Phe Ala Gly
                100                 105                 110

Leu Asp Ala Asp Arg Tyr Asn Met Ala Val Asn Asn Leu Ser Tyr Thr
            115                 120                 125

Lys Glu Arg Ala Glu Lys Tyr Leu Tyr Ala Ala Pro Ile Ala Gln Asn
        130                 135                 140

Pro Asn Val Leu Val Val Lys Lys Asp Asp Ser Ser Ile Lys Ser Leu
145                 150                 155                 160

Asp Asp Ile Gly Gly Lys Ser Thr Glu Val Val Gln Ala Thr Thr Ser
                165                 170                 175

Ala Lys Gln Leu Glu Ala Tyr Asn Ala Glu His Thr Asp Asn Pro Thr
            180                 185                 190

Ile Leu Asn Tyr Thr Lys Ala Asp Leu Gln Gln Ile Met Val Arg Leu
        195                 200                 205

Ser Asp Gly Gln Phe Asp Tyr Lys Ile Phe Asp Lys Ile Gly Val Glu
210                 215                 220

Thr Val Ile Lys Asn Gln Gly Leu Asp Asn Leu Lys Val Ile Glu Leu
225                 230                 235                 240

Pro Ser Asp Gln Gln Pro Tyr Val Tyr Pro Leu Leu Ala Gln Gly Gln
                245                 250                 255

Asp Glu Leu Lys Ser Phe Val Asp Lys Arg Ile Lys Glu Leu Tyr Lys
            260                 265                 270

Asp Gly Thr Leu Glu Lys Leu Ser Lys Gln Phe Phe Gly Asp Thr Tyr
        275                 280                 285

Leu Pro Ala Glu Ala Asp Ile Lys Gly Gly Asp Gln Asn Ala Thr Gly
290                 295                 300

Gly His His His His His His His His
305                 310                 315

<210> SEQ ID NO 9
<211> LENGTH: 266
<212> TYPE: PRT
<213> ORGANISM: Artificial Sequence
<220> FEATURE:
<223> OTHER INFORMATION: Sp0148 amino acid sequence

<400> SEQUENCE: 9

Ala Ala Leu Ala Leu Val Ala Ala Gly Val Leu Ala Ala Cys Ser Gly
1               5                   10                  15

Gly Ala Lys Lys Glu Gly Glu Ala Ala Ser Lys Lys Glu Ile Ile Val
            20                  25                  30

Ala Thr Asn Gly Ser Pro Lys Pro Phe Ile Tyr Glu Glu Asn Gly Glu
        35                  40                  45

Leu Thr Gly Tyr Glu Ile Glu Val Val Arg Ala Ile Phe Lys Asp Ser
50                  55                  60

Asp Lys Tyr Asp Val Lys Phe Glu Lys Thr Glu Trp Ser Gly Val Phe
65                  70                  75                  80

Ala Gly Leu Asp Ala Asp Arg Tyr Asn Met Ala Val Asn Asn Leu Ser
                85                  90                  95

Tyr Thr Lys Glu Arg Ala Glu Lys Tyr Leu Tyr Ala Ala Pro Ile Ala
            100                 105                 110

Gln Asn Pro Asn Val Leu Val Val Lys Lys Asp Asp Ser Ser Ile Lys
        115                 120                 125

Ser Leu Asp Asp Ile Gly Gly Lys Ser Thr Glu Val Val Gln Ala Thr
    130                 135                 140
```

-continued

Thr Ser Ala Lys Gln Leu Glu Ala Tyr Asn Ala Glu His Thr Asp Asn
145                 150                 155                 160

Pro Thr Ile Leu Asn Tyr Thr Lys Ala Asp Leu Gln Gln Ile Met Val
            165                 170                 175

Arg Leu Ser Asp Gly Gln Phe Asp Tyr Lys Ile Phe Asp Lys Ile Gly
            180                 185                 190

Val Glu Thr Val Ile Lys Asn Gln Gly Leu Asp Asn Leu Lys Val Ile
            195                 200                 205

Glu Leu Pro Ser Asp Gln Gln Pro Tyr Val Tyr Pro Leu Leu Ala Gln
            210                 215                 220

Gly Gln Asp Glu Leu Lys Ser Phe Val Asp Lys Arg Ile Lys Glu Leu
225                 230                 235                 240

Tyr Lys Asp Gly Thr Leu Glu Lys Leu Ser Lys Gln Phe Phe Gly Asp
            245                 250                 255

Thr Tyr Leu Pro Ala Glu Ala Asp Ile Lys
            260                 265

<210> SEQ ID NO 10
<211> LENGTH: 713
<212> TYPE: PRT
<213> ORGANISM: Artificial Sequence
<220> FEATURE:
<223> OTHER INFORMATION: Campylobacter jejuni PglB amino acid sequence

<400> SEQUENCE: 10

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
            35                  40                  45

Met Ile Ile Ser Asn Asp Gly Tyr Ala Phe Ala Glu Gly Ala Arg Asp
50                  55                  60

Met Ile Ala Gly Phe His Gln Pro Asn Asp Leu Ser Tyr Tyr Gly Ser
65                  70                  75                  80

Ser Leu Ser Thr Leu Thr Tyr Trp Leu Tyr Lys Ile Thr Pro Phe Ser
            85                  90                  95

Phe Glu Ser Ile Val Leu Tyr Met Ser Thr Phe Leu Ser Ser Leu Val
            100                 105                 110

Val Ile Pro Ile Ile Leu Leu Ala Asn Glu Tyr Lys Arg Pro Leu Met
            115                 120                 125

Gly Phe Val Ala Ala Leu Leu Ala Ser Ile Ala Asn Ser Tyr Tyr Asn
            130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
            165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
            210                 215                 220

Ala Val Ile Ser Ser Ser Leu Thr Leu Ser Asn Ile Ala Trp Phe Tyr
225                 230                 235                 240

```
Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Val Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
    290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Ala Trp Leu Leu Arg Lys His Lys Ser
            340                 345                 350

Met Ile Met Ala Leu Pro Ile Leu Val Leu Gly Phe Leu Ala Leu Lys
        355                 360                 365

Gly Gly Leu Arg Phe Thr Ile Tyr Ser Val Pro Val Met Ala Leu Gly
    370                 375                 380

Phe Gly Phe Leu Leu Ser Glu Phe Lys Ala Ile Leu Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
    450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Leu Gln Asn Asp Ile Leu Lys Thr Asp Ile Leu Gln Ala
        515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ala Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Phe Arg Ser Phe Lys Ile
    610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
```

```
              660                 665                 670
Leu Met Asp Lys Thr Met Phe Asn Ser Ala Tyr Val Gln Met Phe Phe
            675                 680                 685

Leu Gly Asn Tyr Asp Lys Asn Leu Phe Asp Ser Val Ile Asn Ser Arg
        690                 695                 700

Asp Ala Lys Val Phe Lys Leu Lys Ile
705                 710

<210> SEQ ID NO 11
<211> LENGTH: 5
<212> TYPE: PRT
<213> ORGANISM: Artificial Sequence
<220> FEATURE:
<223> OTHER INFORMATION: glycosylation sequon recognised by
      Campylobacter jejuni PglB
<220> FEATURE:
<221> NAME/KEY: MISC_FEATURE
<222> LOCATION: (1)..(1)
<223> OTHER INFORMATION: Xaa = D or E
<220> FEATURE:
<221> NAME/KEY: MISC_FEATURE
<222> LOCATION: (2)..(2)
<223> OTHER INFORMATION: Xaa = Any amino acid except P
<220> FEATURE:
<221> NAME/KEY: MISC_FEATURE
<222> LOCATION: (4)..(4)
<223> OTHER INFORMATION: Xaa = Any amino acid except P
<220> FEATURE:
<221> NAME/KEY: MISC_FEATURE
<222> LOCATION: (5)..(5)
<223> OTHER INFORMATION: Xaa = S or T

<400> SEQUENCE: 11

Xaa Xaa Asn Xaa Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: glycosylation sequon

<400> SEQUENCE: 12

Asp Gln Asn Ala Thr
1               5

<210> SEQ ID NO 13
<211> LENGTH: 21
<212> TYPE: PRT
<213> ORGANISM: Artificial Sequence
<220> FEATURE:
<223> OTHER INFORMATION: DsbA leader sequence

<400> SEQUENCE: 13

Met Lys Lys Ile Trp Leu Ala Leu Ala Gly Leu Val Leu Ala Phe Ser
1               5                   10                  15

Ala Ser Ala Ala Gln
            20

<210> SEQ ID NO 14
<211> LENGTH: 10
<212> TYPE: PRT
<213> ORGANISM: Artificial Sequence
<220> FEATURE:
<223> OTHER INFORMATION: purification tag

<400> SEQUENCE: 14
```

```
Met Arg Gly Ser His His His His His His
1               5                   10

<210> SEQ ID NO 15
<211> LENGTH: 8
<212> TYPE: PRT
<213> ORGANISM: Artificial Sequence
<220> FEATURE:
<223> OTHER INFORMATION: purification tag

<400> SEQUENCE: 15

Asp Tyr Lys Asp Asp Asp Asp Lys
1               5

<210> SEQ ID NO 16
<211> LENGTH: 15
<212> TYPE: PRT
<213> ORGANISM: Artificial Sequence
<220> FEATURE:
<223> OTHER INFORMATION: purification tag

<400> SEQUENCE: 16

Lys Glu Thr Ala Ala Ala Lys Phe Glu Arg Gln His Met Asp Ser
1               5                   10                  15

<210> SEQ ID NO 17
<211> LENGTH: 5
<212> TYPE: PRT
<213> ORGANISM: Artificial Sequence
<220> FEATURE:
<223> OTHER INFORMATION: purification tag

<400> SEQUENCE: 17

Arg Arg Arg Arg Arg
1               5

<210> SEQ ID NO 18
<211> LENGTH: 6
<212> TYPE: PRT
<213> ORGANISM: Artificial Sequence
<220> FEATURE:
<223> OTHER INFORMATION: purification tag

<400> SEQUENCE: 18

Arg Arg Arg Arg Arg Arg
1               5

<210> SEQ ID NO 19
<211> LENGTH: 6
<212> TYPE: PRT
<213> ORGANISM: Artificial Sequence
<220> FEATURE:
<223> OTHER INFORMATION: purification tag

<400> SEQUENCE: 19

His His His His His His
1               5

<210> SEQ ID NO 20
<211> LENGTH: 7
<212> TYPE: PRT
<213> ORGANISM: Artificial Sequence
<220> FEATURE:
<223> OTHER INFORMATION: purification tag

<400> SEQUENCE: 20
```

```
His His His His His His His
1               5

<210> SEQ ID NO 21
<211> LENGTH: 8
<212> TYPE: PRT
<213> ORGANISM: Artificial Sequence
<220> FEATURE:
<223> OTHER INFORMATION: purification tag

<400> SEQUENCE: 21

His His His His His His His His
1               5

<210> SEQ ID NO 22
<211> LENGTH: 9
<212> TYPE: PRT
<213> ORGANISM: Artificial Sequence
<220> FEATURE:
<223> OTHER INFORMATION: purification tag

<400> SEQUENCE: 22

His His His His His His His His His
1               5

<210> SEQ ID NO 23
<211> LENGTH: 10
<212> TYPE: PRT
<213> ORGANISM: Artificial Sequence
<220> FEATURE:
<223> OTHER INFORMATION: purification tag

<400> SEQUENCE: 23

His His His His His His His His His His
1               5                   10

<210> SEQ ID NO 24
<211> LENGTH: 4
<212> TYPE: PRT
<213> ORGANISM: Artificial Sequence
<220> FEATURE:
<223> OTHER INFORMATION: purification tag

<400> SEQUENCE: 24

Cys Cys Cys Cys
1

<210> SEQ ID NO 25
<211> LENGTH: 11
<212> TYPE: PRT
<213> ORGANISM: Artificial Sequence
<220> FEATURE:
<223> OTHER INFORMATION: purification tag

<400> SEQUENCE: 25

Phe Phe Phe Phe Phe Phe Phe Phe Phe Phe Phe
1               5                   10

<210> SEQ ID NO 26
<211> LENGTH: 5
<212> TYPE: PRT
<213> ORGANISM: Artificial Sequence
<220> FEATURE:
<223> OTHER INFORMATION: purification tag

<400> SEQUENCE: 26

Asp Asp Asp Asp Asp
```

```
1               5
```

<210> SEQ ID NO 27
<211> LENGTH: 6
<212> TYPE: PRT
<213> ORGANISM: Artificial Sequence
<220> FEATURE:
<223> OTHER INFORMATION: purification tag

<400> SEQUENCE: 27

```
Asp Asp Asp Asp Asp Asp
1               5
```

<210> SEQ ID NO 28
<211> LENGTH: 7
<212> TYPE: PRT
<213> ORGANISM: Artificial Sequence
<220> FEATURE:
<223> OTHER INFORMATION: purification tag

<400> SEQUENCE: 28

```
Asp Asp Asp Asp Asp Asp Asp
1               5
```

<210> SEQ ID NO 29
<211> LENGTH: 8
<212> TYPE: PRT
<213> ORGANISM: Artificial Sequence
<220> FEATURE:
<223> OTHER INFORMATION: purification tag

<400> SEQUENCE: 29

```
Asp Asp Asp Asp Asp Asp Asp Asp
1               5
```

<210> SEQ ID NO 30
<211> LENGTH: 9
<212> TYPE: PRT
<213> ORGANISM: Artificial Sequence
<220> FEATURE:
<223> OTHER INFORMATION: purification tag

<400> SEQUENCE: 30

```
Asp Asp Asp Asp Asp Asp Asp Asp Asp
1               5
```

<210> SEQ ID NO 31
<211> LENGTH: 10
<212> TYPE: PRT
<213> ORGANISM: Artificial Sequence
<220> FEATURE:
<223> OTHER INFORMATION: purification tag

<400> SEQUENCE: 31

```
Asp Asp Asp Asp Asp Asp Asp Asp Asp Asp
1               5                   10
```

<210> SEQ ID NO 32
<211> LENGTH: 11
<212> TYPE: PRT
<213> ORGANISM: Artificial Sequence
<220> FEATURE:
<223> OTHER INFORMATION: purification tag

<400> SEQUENCE: 32

```
Asp Asp Asp Asp Asp Asp Asp Asp Asp Asp Asp
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: purification tag

<400> SEQUENCE: 33

Asp Asp Asp Asp Asp Asp Asp Asp Asp Asp Asp Asp
1               5                   10

<210> SEQ ID NO 34
<211> LENGTH: 13
<212> TYPE: PRT
<213> ORGANISM: Artificial Sequence
<220> FEATURE:
<223> OTHER INFORMATION: purification tag

<400> SEQUENCE: 34

Asp Asp Asp Asp Asp Asp Asp Asp Asp Asp Asp Asp Asp
1               5                   10

<210> SEQ ID NO 35
<211> LENGTH: 14
<212> TYPE: PRT
<213> ORGANISM: Artificial Sequence
<220> FEATURE:
<223> OTHER INFORMATION: purification tag

<400> SEQUENCE: 35

Asp Asp Asp Asp Asp Asp Asp Asp Asp Asp Asp Asp Asp Asp
1               5                   10

<210> SEQ ID NO 36
<211> LENGTH: 15
<212> TYPE: PRT
<213> ORGANISM: Artificial Sequence
<220> FEATURE:
<223> OTHER INFORMATION: purification tag

<400> SEQUENCE: 36

Asp Asp Asp Asp Asp Asp Asp Asp Asp Asp Asp Asp Asp Asp Asp
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: purification tag

<400> SEQUENCE: 37

Asp Asp Asp Asp Asp Asp Asp Asp Asp Asp Asp Asp Asp Asp Asp Asp
1               5                   10                  15

<210> SEQ ID NO 38
<211> LENGTH: 8
<212> TYPE: PRT
<213> ORGANISM: Artificial Sequence
<220> FEATURE:
<223> OTHER INFORMATION: strep-tag II

<400> SEQUENCE: 38

Trp Ser His Pro Gln Phe Glu Lys
1               5

```
<210> SEQ ID NO 39
<211> LENGTH: 10
<212> TYPE: PRT
<213> ORGANISM: Artificial Sequence
<220> FEATURE:
<223> OTHER INFORMATION: c-myc tag

<400> SEQUENCE: 39

Glu Gln Lys Leu Ile Ser Glu Glu Asp Leu
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Cruz tag 09

<400> SEQUENCE: 40

Met Lys Ala Glu Phe Arg Arg Gln Glu Ser Asp Arg
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Cruz tag 22

<400> SEQUENCE: 41

Met Arg Asp Ala Leu Asp Arg Leu Asp Arg Leu Ala
1               5                   10
```